US006663681B2

(12) United States Patent
Kindig et al.

(10) Patent No.: US 6,663,681 B2
(45) Date of Patent: Dec. 16, 2003

(54) METHOD FOR THE PRODUCTION OF HYDROGEN AND APPLICATIONS THEREOF

(75) Inventors: James Kelly Kindig, Phoenix, AZ (US); Boyd R. Davis, Kingston (CA); Robert R. Odle, Greenville, SC (US); Thomas E. Weyand, New Brighton, PA (US)

(73) Assignee: Alchemix Corporation, Carefree, AZ (US)

( * ) Notice: Subject to any disclaimer, the term of this patent is extended or adjusted under 35 U.S.C. 154(b) by 0 days.

(21) Appl. No.: 10/085,436

(22) Filed: Feb. 28, 2002

(65) Prior Publication Data

US 2003/0072705 A1 Apr. 17, 2003

Related U.S. Application Data

(63) Continuation-in-part of application No. 09/800,769, filed on Mar. 6, 2001, and a continuation-in-part of application No. 09/800,423, filed on Mar. 6, 2001, and a continuation-in-part of application No. 09/800,421, filed on Mar. 6, 2001, and a continuation-in-part of application No. 09/800,434, filed on Mar. 6, 2001.

(51) Int. Cl.$^7$ .............................. C01B 3/08; C01B 3/32; C01C 1/04
(52) U.S. Cl. ................... 48/127.5; 48/210; 423/359; 423/657; 423/658
(58) Field of Search ............................. 423/657, 658, 423/359; 48/127.5, 210

(56) References Cited

U.S. PATENT DOCUMENTS

| | | |
|---|---|---|
| 1,050,902 A | 1/1913 | Acker |
| 1,345,905 A | 7/1920 | Abbott |
| 3,031,287 A | 4/1962 | Benson et al. |
| 3,700,584 A | 10/1972 | Johanson et al. |
| 3,733,187 A | 5/1973 | Feldmann ............... 48/209 |
| 3,821,362 A | 6/1974 | Spacil ................... 423/657 |
| 3,880,987 A | 4/1975 | Nahas ................... 423/657 |
| 3,971,639 A | 7/1976 | Matthews ............... 48/202 |
| 3,979,505 A | 9/1976 | Seitzer .................. 423/657 |
| 4,005,994 A | 2/1977 | Feldmann ............... 48/111 |
| 4,072,514 A | 2/1978 | Suzuki .................. 75/168 |
| 4,088,740 A | 5/1978 | Gaines .................. 423/359 |
| 4,095,959 A | 6/1978 | Kiinstle et al. .......... 48/73 |
| 4,126,668 A | 11/1978 | Erickson ............... 423/657 |
| 4,152,122 A | 5/1979 | Feldmann ............... 48/111 |
| 4,216,199 A | 8/1980 | Erickson ............... 423/657 |
| 4,298,588 A | 11/1981 | Pinto ................... 423/399 |
| 4,310,503 A | 1/1982 | Erickson ............... 423/657 |
| 4,312,638 A | 1/1982 | Koump .................. 48/197 |
| 4,328,009 A | 5/1982 | Fischer et al. ........... 48/202 |
| 4,343,624 A | 8/1982 | Belke et al. ............ 48/61 |
| 4,555,249 A | 11/1985 | Leas .................... 48/62 |
| 4,600,571 A | 7/1986 | McCarroll et al. ........ 423/363 |
| 4,819,571 A | 4/1989 | Hallett ................. 110/346 |
| 4,842,719 A | 6/1989 | MacArthur et al. ....... 208/421 |
| 5,050,511 A | 9/1991 | Hallett et al. .......... 110/346 |
| 5,158,982 A | 10/1992 | Stapp ................... 521/41 |
| 5,158,983 A | 10/1992 | Stapp ................... 521/41 |
| 5,451,297 A | 9/1995 | Roy .................... 201/25 |
| 5,478,370 A | * 12/1995 | Spangler ................ 252/373 |

FOREIGN PATENT DOCUMENTS

| | | | |
|---|---|---|---|
| JP | 19910085494199910417 | 9/1992 | ............ C22B/1/02 |
| JP | 04-310392 | 3/1994 | ............ C01B/3/10 |
| JP | 6-247702 | 9/1994 | ............ C01B/3/02 |

OTHER PUBLICATIONS

H2 From Biosyngas Via Iron Reduction And Oxidation, John Straus and Peter Terry, H. Power–Corp., Belleville, NJ 07109 (no date).
Hydrogen From Coal Via Tin Redox: Energy Related Invention Program INV #3, by D.C. Erickson, Feb. 1981.

* cited by examiner

Primary Examiner—Wayne A. Langel
(74) Attorney, Agent, or Firm—Marsh Fischmann & Breyfogle LLP

(57) ABSTRACT

A method for the production of hydrogen gas. The hydrogen gas is formed by steam reduction using a metal/metal oxide couple to remove oxygen from water. Steam is contacted with a molten metal mixture including a first reactive metal such as iron dissolved in a diluent metal such as tin. The reactive metal oxidizes to a metal oxide, forming a hydrogen gas and the metal oxide can then be reduced back to the metal for further production of hydrogen without substantial movement of the metal or metal oxide to a second reactor.

87 Claims, 7 Drawing Sheets

METHOD FOR THE PRODUCTION OF HYDROGEN AND APPLICATIONS THEREOF

CROSS-REFERENCE TO RELATED APPLICATIONS

This application is a continuation-in-part of U.S. patent application Ser. No. 09/800,769 filed Mar. 6, 2001, U.S. patent application Ser. No. 09/800,423 filed Mar. 6, 2001, U.S. patent application Ser. No. 09/800,421 filed Mar. 6, 2001, and U.S. patent application Ser. No. 09/800,434 filed Mar. 6, 2001, each of which is incorporated herein by reference in its entirety.

STATEMENT REGARDING FEDERALLY FUNDED RESEARCH

Not applicable

BACKGROUND OF THE INVENTION

1. Field of the Invention

The present invention is directed to a method for the production of hydrogen gas. More particularly, the present invention is directed to a method for the production of hydrogen gas by steam reduction wherein steam is contacted with molten metal to form a metal oxide and a hydrogen-containing gas stream. The metal oxide can then be reduced back to the metal for further production of hydrogen gas. The hydrogen gas can be used for the generation of energy and in various chemical processes, such as the treatment of coal and the production of ammonia.

2. Description of Related Art

Hydrogen ($H_2$) is a valuable commodity and specialty chemical that is critical to a number of industrial processes including the production of ammonia and the refining of oil. In addition, hydrogen can be converted directly to electricity in fuel cells at efficiencies approaching 80 percent. Water is the sole by-product of hydrogen conversion in fuel cells, and toxic emissions are eliminated. For these reasons, hydrogen is widely considered the fuel of the future.

It is known that hydrogen gas can be produced from many different feedstocks such as natural gas, biomass or water using different techniques such as reformation, gasification or electrolysis. The most common methods are steam methane reformation (SMR), coal gasification, steam reduction, biomass gasification and pyrolysis, and electrolysis.

Steam methane reformation is believed to be the most economical and commercially viable process that is presently available. In the SMR process, methane ($CH_4$) is reacted with steam ($H_2O$) to form a gas stream that includes hydrogen and carbon monoxide (CO). The feedstock is typically natural gas and the cost of the natural gas represents a significant portion of the total production cost.

At least two major difficulties are associated with the SMR method. One difficulty is the dependency of the hydrogen production cost on the price of natural gas. The price of natural gas is highly volatile due to supply/demand issues, which are projected to persist into the future. Secondly, hydrogen produced by SMR is co-mingled with a significant quantity of carbon oxides that can only be partially removed by scrubbing or pressure swing adsorption, both of which are costly. The carbon oxides remaining in SMR hydrogen are detrimental to the catalysts employed in fuel cells and in the production of ammonia ($NH_3$) from hydrogen.

Hydrogen production by coal gasification is another established commercial technology, but is only economically competitive when natural gas is prohibitively expensive. In the coal gasification process, steam and oxygen ($O_2$) are utilized in the coal gasifier to produce a hydrogen-containing gas. High purity hydrogen can then be extracted from the synthesis gas by a water-gas shift reaction followed by removal of the carbon dioxide ($CO_2$) by pressure swing adsorption or scrubbing. Impurities such as acid gases must also be separated from the hydrogen. Hydrogen can also be formed by the gasification of other hydrocarbons such as residual oil.

The steam reduction method utilizes the oxidation of a metal to strip oxygen from steam (i.e., steam reduction), thereby forming hydrogen gas. This reaction is illustrated by Equation 1.

$$x\text{Me} + y\text{H}_2\text{O} \rightarrow \text{Me}_x\text{O}_y + y\text{H}_2 \tag{1}$$

To complete the cycle in a two-step steam reduction process, the metal oxide must be reduced back to the metal using a reductant. For example, carbon monoxide (CO) has an oxygen affinity that is similar to the oxygen affinity of hydrogen and they are equal at about 812° C. At temperatures above about 812° C., CO has a greater affinity for oxygen than does hydrogen. Thus, if the CO has an oxygen affinity greater than the oxygen affinity of the metal at equilibrium, the CO will reduce the oxide of Equation 1 back to the metal.

$$\text{Me}_x\text{O}_y + y\text{CO} \rightarrow x\text{Me} + y\text{CO}_2 \tag{2}$$

Generally stated, the function of the metal/metal oxide couple is to transfer oxygen from the steam to the reducing gas (CO) without allowing the steam/hydrogen of the hydrogen production step to contact the carbon monoxide/carbon dioxide of the metal oxide reduction step. The metal and metal oxide are not consumed by the overall process.

Oxygen partial pressure ($pO_2$) relates to the facility with which the metal may be oxidized (e.g., by steam) and the oxide may be reduced (e.g., by CO). A related mathematical expression is $pH_2O/pH_2$, which is proportional to the oxygen partial pressure. Also, an equivalent and inversely related quantity is the hydrogen fraction, expressed as:

$$\frac{pH_2}{(pH_2 + pH_2O)} \tag{3}$$

Certain metals react strongly with water, releasing hydrogen. Examples of such metals include: lithium (Li), sodium (Na), potassium (K), rubidium (Rb), cesium (Cs), francium (Fr), beryllium (Be), magnesium (Mg), calcium (Ca), strontium (Sr), barium (Ba), radium (Ra), aluminum (Al), silicon (Si), phosphorus, (P), titanium (Ti), vanadium (V), chromium (Cr), manganese (Mn), yttrium (Y), zirconium (Zr), niobium (Nb), lanthanum (La), hafnium (Hf), tantalum (Ta) and gallium (Ga). The oxygen partial pressure in equilibrium with these metals and their oxides together is extremely low. Once the oxides are formed, they cannot be effectively reduced back to the metal by carbon monoxide. Conversely, there is another group of metals that produce insignificant quantities of hydrogen when reacted with water. Examples of these metals include: nickel (Ni), copper (Cu), ruthenium (Ru), rhodium (Rh), palladium (Pd), silver (Ag), cadmium (Cd), rhenium (Re), osmium (Os), iridium (Ir), platinum (Pt), gold (Au), mercury, (Hg), lead (Pb), bismuth (Bi), selenium (Se) and tellurium (Te). The oxygen partial pressure in equilibrium with these metals and their oxides together is quite high. The oxides, therefore, can be easily reduced by carbon monoxide.

Between the two foregoing groups of metals are other metals characterized by an oxygen affinity that is roughly the same as the oxygen affinity of hydrogen. Included in this intermediate group of metals are: germanium (Ge), iron (Fe), zinc (Zn), tungsten (W), molybdenum (Mo), indium (In), tin (Sn), cobalt (Co) and antimony (Sb). These are elements that readily produce hydrogen from steam wherein the resulting oxide can be reduced by carbon monoxide. That is, these metals have an oxygen affinity such that their equilibrium $pH_2O/pH_2$ is low enough to be practical for the production of hydrogen, yet the metal oxide is readily reduced by carbon at normal pyrometallurgical temperatures (e.g., about 1200° C.). These metals are referred to herein as reactive metals, meaning that both the metal can be oxidized by steam and the metal oxide can be reduced by carbon monoxide.

The steam reduction/iron oxidation process was the primary industrial method for manufacturing hydrogen during the 19th and early 20th centuries. At elevated temperatures, iron strips oxygen from water, leaving pure hydrogen.

$$3Fe+4H_2O \rightarrow Fe_3O_4+4H_2 \quad (4)$$

Excess water is required to maximize hydrogen production from a given amount of iron. After the hydrogen is produced, excess water is condensed leaving an uncontaminated hydrogen gas steam. The reaction products of the steam reduction/iron oxidation process are pure hydrogen and wustite (FeO) and/or magnetite ($Fe_3O_4$). To regenerate the metal, carbon monoxide or carbon captures the oxygen from the iron oxide, forming iron metal and carbon monoxide or carbon dioxide ($CO_2$).

In the early years of hydrogen manufacturing, these two steps were carried out at different locations. The primary cost components for producing hydrogen by this method included the cost of the iron used minus the value received for the iron oxide produced and the cost of producing the excess steam required to drive the reaction (a function of temperature). This cost was reduced by the benefits derived from recovering excess energy from the steam. There are numerous examples in the prior art of the foregoing method.

U.S. Pat. No. 1,345,905 by Abbott discloses the production of hydrogen from steam by oxidation of iron using multiple reactors. In a four-reactor configuration, one reactor is used for iron oxidation (hydrogen production), two are used for iron oxide reduction and the fourth is used for preheating the reactants. Gas flows can be switched among the reactors for the continuous production of hydrogen.

U.S. Pat. No. 4,343,624 by Belke et al. discloses a 3-stage hydrogen production method and apparatus utilizing steam reduction as the hydrogen source. In a first stage, a low BTU gas containing hydrogen and carbon monoxide is formed from a feedstock such as coal. The low BTU gas is then reacted in a second stage with magnetite to form iron, carbon dioxide and steam. The steam and iron are then reacted in a third stage to form hydrogen gas and magnetite. It is disclosed that the magnetite can be returned to the second stage for use in the reduction reaction, such as by continuously returning the magnetite to the second stage reactor via a feed conduit. At least one of the stages takes place in a rotating fluidized bed reactor.

U.S. Pat. No. 4,555,249 by Leas discloses a gas fractionating unit that contains a reagent powder, such as an iron alloy, having a significant weight difference between the reduced form and the oxidized form. The unit includes two zones for containing the reagent powder, an oxidation zone and a reduction zone, wherein hydrogen gas is extracted from the oxidation zone. As the reagent powder is converted from the oxidized to the reduced form, the weight of the powder increases and the change in weight is utilized to transfer the reduced powder to the oxidation zone while moving the oxidized powder to the reduction zone.

The article "$H_2$ from Biosyngas via Iron Reduction and Oxidation", by Straus et al., discloses a method for hydrogen production from biosyngas. The biosyngas, which includes $H_2$, CO, $H_2O$, and $CO_2$ with traces of $N_2$ and $CH_4$, is used to reduce magnetite to iron. The iron is then cooled and fed to a hydrogen gas generator where the iron is contacted with steam to form hydrogen by steam reduction. The iron oxide is then cooled and returned to the metal oxide reduction reactor for reaction with the biosyngas.

Disadvantages of the steam reduction process utilizing iron include that the reaction of solid iron with steam produces an oxide layer, which inhibits additional steam from reacting with iron beneath the oxide layer and therefore the rate of reaction is limited by the rate of gas-diffusion through the oxide layer. Also, the rate of reaction is dependent upon the surface area of the iron available for the reaction. High surface area, however, is equated with small particle size, and small particles are expensive to process. Further, there are difficulties associated with reducing the iron oxide. One method for reducing the iron oxide includes smelting of the oxide and therefore carries the disadvantage of high temperature due to the high melting point of iron (1538° C.). In another method, the iron oxide is reduced to the metal in the solid state by carbon and/or reducing gas. This latter process, however, is inefficient and kinetically difficult. Excluding reduction in the solid state, for each ton of hydrogen produced, a minimum of 20.8 tons of iron and 28.7 tons of magnetite must physically be moved from one reactor (metal oxidation) to another (metal reduction).

Other metals besides iron have been used for steam reduction processes. U.S. Pat. No. 1,050,902 by Acker discloses the use of tin or zinc in a steam reduction process to form hydrogen and the regeneration of the metal by reduction of the metal oxide with coal.

U.S. Pat. No. 3,821,362 by Spacil illustrates the use of $Sn/SnO_2$ to form hydrogen. Molten tin is atomized and contacted with steam to form $SnO_2$ and hydrogen gas. The $SnO_2$ is then contacted with a producer gas composed of $H_2$, $N_2$ and CO, which is formed by contacting powdered coal with air. The $SnO_2$ is reduced to liquid tin, which is then transferred back to the first reactor. A similar method for hydrogen production is illustrated in U.S. Pat. No. 3,979,505 by Seitzer.

U.S. Pat. Nos. 4,310,503 and 4,216,199 by Erickson disclose a comprehensive investigation of the potential of tin to act as the carrier of the oxygen from steam to carbon dioxide. An extension of this work is also reported in "Hydrogen from Coal via Tin Redox" by Erickson, prepared for the Office of Energy Related Inventions, U.S. Department of Energy (February 1981).

Erickson reports that the yield of hydrogen obtainable from a given quantity of carbonaceous reducing composition can be increased by using a multi-staged process wherein successive stages are arranged in order of increasing equilibrium $pH_2/pH_2O$ for the metal oxidation reaction with steam. Among the substances used as intermediates (i.e., metal/metal-oxide couples) were pure solids such as iron, wustite (FeO), tungsten dioxide ($WO_2$), molybdenum and germanium; pure liquids such as tin and indium; and dissolved liquids such as tin, indium, germanium, zinc and iron, where dissolved means that the intermediate is present at less than unit activity. The effect of employing a dissolved liquid is that the oxygen partial pressure is increased (i.e., the hydrogen fraction is decreased) and less hydrogen is produced. Erickson discloses that suitable solvents for the dissolved liquids may be selected from one or more of the non-reactive metals that have a high oxygen partial pressure, for example copper, lead and nickel. It is also disclosed that tin, a reactive metal, can serve as a solvent for indium.

When forming hydrogen by using tin in a steam reduction process, the first reaction is:

$$Sn + 2H_2O \rightarrow SnO_2 + 2H_2 \qquad (5)$$

To secure reasonable kinetics for the above reaction, a temperature above about 900° C. is required, and tin is a liquid at that temperature ($T_m$=232° C.). At such high temperatures thermodynamics dictate that a large excess of steam is required in order for the reaction to proceed. The need for a large excess of steam creates a number of problems. Heat must be recovered for the process to be economical, including the heat of evaporation of the water to form the steam. Technically, most of this heat recovery is possible, although doing so requires additional capital. Also, a large excess of steam must physically contact the tin, such as by being bubbled through the liquid tin. Practically, such contact is possible only if the steam and reactor are operated under considerable pressure and, generally, processes that operate at very high pressures are quite expensive.

For example, the production of one ton of hydrogen requires the reaction of 8.94 tons of steam with 29.4 tons of tin (stoichiometric calculations). Additionally, the production of one ton of hydrogen at 900° C. requires 35.7 tons of steam to satisfy the thermodynamic requirement. If this total steam requirement (44.6 tons) is passed through the stoichiometric quantity of tin at atmospheric pressure, the velocity of the steam through the space that otherwise would be occupied by the tin must be in excess of 100 meters per second. This yields a nominal residence time of less than ¹⁄₁₀₀ of a second. Even if system pressure is raised to 100 atmospheres, only 0.85 seconds are available for the reaction to approach equilibrium. An amount of tin in excess of the stoichiometric requirement can be used, and the effect of a larger weight (larger volume) of tin is to increase the nominal residence time. This approach of increasing nominal residence time is expensive, however, because of the increased size of the tin-steam reactor and increased inventory of tin required.

Thus, there remains a need for a method for producing hydrogen that is technically sound and economically viable. Both the steam/iron and steam/tin processes are technically viable. Neither, however, meets the requirement for economic viability. The steam/iron process is not satisfactory because: (1) the production of hydrogen is diffusion controlled; (2) the cost of moving the metal is high; and (3) the difficulty (cost) of reducing the iron is high. The steam/tin process fails the economic viability requirement because of poor kinetics at low temperatures (below about 800° C.) and poor thermodynamics at higher temperatures. The consequence of poor thermodynamics is the requirement that large amounts of steam be processed through the molten metal, which increases the difficulty and cost of the process. Due to these and other factors, the present inventors are not aware of a commercial facility that is practicing the steam reduction method, despite the high demand for hydrogen gas.

BRIEF SUMMARY OF THE INVENTION

According to one embodiment of the present invention, a method for the production of a hydrogen-containing gas stream is provided. The method includes the steps of generating steam and contacting the steam with a molten metal mixture having at least about 20 weight percent iron dissolved in a diluent metal, wherein at least a portion of the iron is oxidized to a metal oxide and at least a portion of the steam is reduced to form a hydrogen-containing gas stream. Preferably, the diluent metal is tin. By contacting the steam with iron that is dissolved in a diluent metal, the problems associated with thermodynamic and kinetic limitations inherent in prior steam reduction methods are reduced.

According to another embodiment, a method for the production of a hydrogen-containing gas is provided wherein steam is generated and is contacted with a molten metal mixture at a temperature of at least about 1100° C. The molten metal mixture includes a reactive metal dissolved in a diluent metal wherein the reactive metal is oxidized and the steam is reduced to form hydrogen. The use of temperatures of at least about 1100° C. for the molten metal mixture enables the production of hydrogen under favorable thermodynamic and kinetic conditions.

According to another embodiment, a method for the production of a hydrogen-containing gas stream is provided that includes the steps of generating steam, contacting the steam with a molten metal mixture in a reactor, wherein reactive metal-contaning particles are dispersed in the molten metal mixture. The reactive-metal containing particles advantageously supply additional reactive metal to the molten metal mixture as the reactive metal is oxidized by the steam.

According to another embodiment, a method for the production of a hydrogen-containing gas stream is provided that includes the steps of contacting steam with a molten metal mixture in a reactor, the molten metal mixture including a reactive metal dissolved in a diluent metal. The reactive metal is oxidized to a metal oxide by the steam. The metal oxide is then reduced back to the reactive metal within the reactor.

The hydrogen-containing gas stream produced in according with the foregoing can be used in a variety of processes and is particularly suited to the treatment of carbon-bearing substances such as coal or waste products and to the manufacture of chemicals such as ammonia.

DETAILED DESCRIPTION OF THE INVENTION

Figure 1:
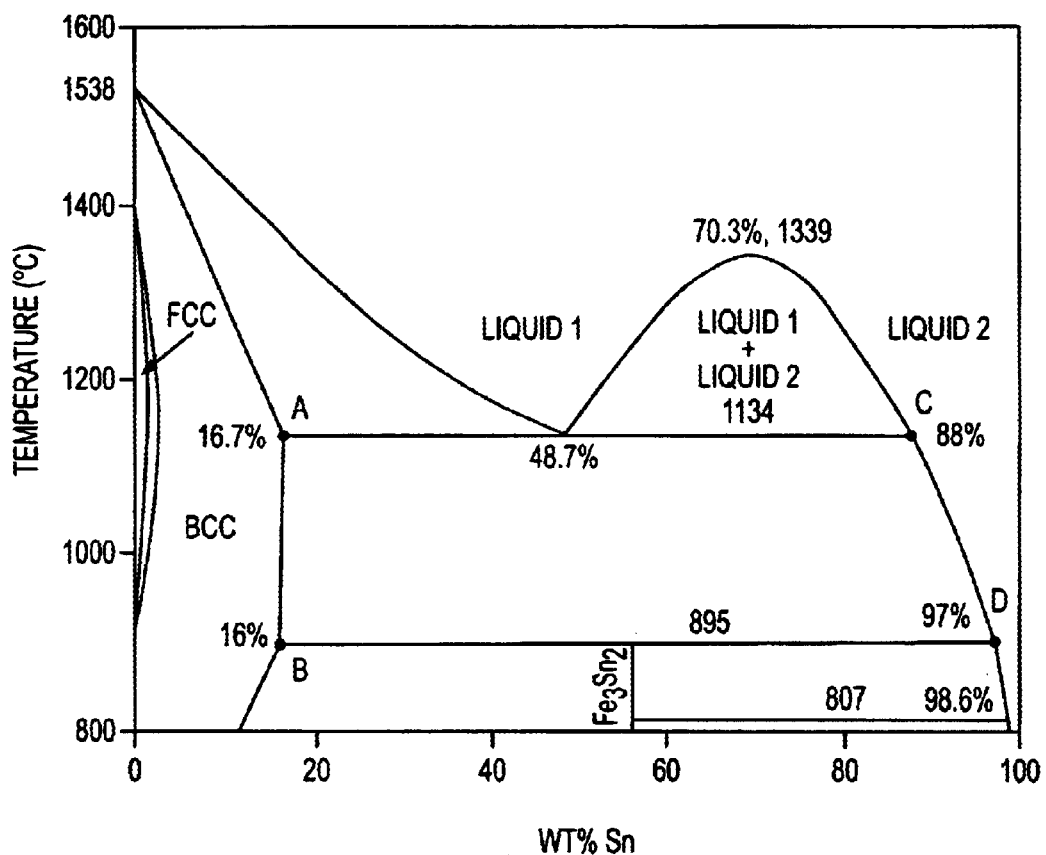
FIG. 1 illustrates a binary phase diagram for a tin-iron metal mixture that is useful in accordance with the present invention.

According to the present invention, hydrogen gas ($H_2$) is formed by contacting steam ($H_2O$) with a molten metal mixture that includes at least a first reactive metal that is at least partially dissolved in at least one diluent metal. The diluent metal may also be reactive with the steam, but is, by definition, less reactive with steam than the reactive metal. Thus, the oxygen from the steam preferentially reacts with the reactive metal to oxidize the reactive metal to a metal oxide and reduce a portion of the steam to form a hydrogen-containing gas stream that will also include excess steam. In a preferred embodiment, hydrogen production continues until the concentration of the dissolved reactive metal in the molten metal mixture is reduced to a minimum concentration that is dictated by economics, at which point the injection of steam is terminated. Then, a reductant is introduced into the reactor under conditions of intense mixing, such as by using a top-submerged lance. Under these conditions, the metal oxide is chemically reduced back to the reactive metal, which re-dissolves into the molten metal mixture. By switching the flow of the steam and the reductant between two or more reactors, hydrogen can be produced substantially continuously. The method of the present invention provides significant advantages over steam reduction methods of the prior art.

To initiate the production of hydrogen, steam is contacted with a molten metal mixture that includes at least a first reactive metal and at least a first diluent metal. The reactive metal is, by definition, more reactive with steam than the diluent metal. The reactive metal preferably has an oxygen affinity that is similar to the oxygen affinity of hydrogen and reacts with the steam to form a metal oxide. For example, the reactive metal can be selected from germanium (Ge), iron (Fe), zinc (Zn), tungsten (W), molybdenum (Mo), indium (In), tin (Sn), cobalt (Co) and antimony (Sb). The molten metal mixture can include one or more reactive metals. The reactive metal preferably should: (1) be soluble in the diluent metal(s); (2) have a very low vapor pressure at the oxidation/reduction temperature(s); and (3) produce one or more oxides when reacted with steam that also has a very low vapor pressure at the oxidation/reduction temperature (s). A particularly preferred reactive metal according to the present invention is iron and according to one embodiment the reactive metal in the molten metal mixture consists essentially of iron.

The reactive metal is at least partially dissolved within a second metal, or mixture of metals. The metal into which the reactive metal is dissolved is referred to herein as the diluent metal. The diluent metal may also be reactive with steam, in which case it can be selected from the group of reactive metals disclosed hereinabove, provided that the diluent metal is less reactive than the reactive metal. Alternatively, the diluent metal may be selected from the metals wherein the oxygen partial pressure ($pO_2$) in equilibrium with the metal and oxides together is relatively high. These include nickel (Ni), copper (Cu), ruthenium (Ru), rhodium (Rh), palladium (Pd), silver (Ag), cadmium (Cd), rhenium (Re), osmium (Os), iridium (Ir), platinum (Pt), gold (Au), mercury, (Hg), lead (Pb), bismuth (Bi), selenium (Se) and tellurium (Te). More than one diluent metal can be utilized in the molten metal mixture. The diluent metal should not be a metal wherein the oxygen partial pressure in equilibrium with the metal and metal oxide together is extremely low.

Preferably, the diluent metal should: (1) combine with the reactive metal to be liquid in the temperature range of 400° C. to 1300° C.; (2) have a very low vapor pressure over this temperature range; and (3) have the capacity to hold the reactive metal in solution. According to a preferred embodiment of the present invention, the diluent metal is tin and in one embodiment, the diluent metal consists essentially of tin. However, the molten metal mixture can also include additional diluent metals, particularly copper and nickel.

A particularly preferred molten metal mixture for steam reduction according to the present invention includes iron as the reactive metal and tin as the diluent metal. Iron has a high solubility in molten tin at elevated temperatures and the melting temperature of the mixture is substantially lower than the melting temperature of pure iron (1538° C.). Although tin is also reactive with steam, it is less reactive than iron.

Due to thermodynamics, steam reduction reactions to form hydrogen gas require an excess of steam above the stoichiometric requirement. The total steam requirement (the mass ratio of steam required to hydrogen produced) for iron is much less than for tin at all temperatures and iron will preferentially oxidize in the molten metal mixture. While not wishing to be bound by any theory, it is believed that some reactive tin is oxidized to tin oxide, but is immediately reduced back to tin:

$$2H_2O + Sn \rightarrow SnO_2 + 2H_2 \quad (6)$$

$$SnO_2 + 2Fe \rightarrow 2FeO + Sn \quad (7)$$

$$Net: 2H_2O + Fe \rightarrow FeO + 2H_2 \quad (8)$$

The thermodynamic steam requirement for tin at 660° C. is approximately equal to the thermodynamic steam requirement for iron at 1200° C. However, the production of hydrogen using tin as a reactive metal at 660° C. is not practical since the kinetics (i.e., the reaction rate) are very poor and therefore very long residence times (i.e., the time that the steam is in contact with the tin) are required.

At 1200° C., the kinetics for both tin and iron are excellent. The steam requirement for tin, however, is much greater than for iron. According to the present invention, the residence time that the steam is in contact with the reactive metal is increased by the use of a diluent metal. For purposes of illustration, a comparison of the thermodynamic steam requirement and the nominal residence times at a temperature of 1200° C. and various pressures for a dissolved iron embodiment of the present invention (50 wt. % iron in tin) compared to pure tin is illustrated in Tables 1 and 2. Table 1 illustrates the total steam required to produce one ton of hydrogen at 1200° C.

TABLE 1

| System | $pH_2/pH_2O$ | Stoichiometric Steam (tons) | Thermodynamic Steam (tons) | Total Steam (tons) |
|---|---|---|---|---|
| Pure Tin | 0.118 | 8.94 | 76.01 | 84.94 |
| Tin/Iron (50:50 by weight) | 1.732 | 8.94 | 12.21 | 21.15 |

Table 2 illustrates the nominal residence times of the steam at a production rate of 4.439 tons of hydrogen per hour.

TABLE 2

| System | Total Steam (m³/hr) | Melt Volume (m³) | Nominal Residence Time (seconds) | | |
| --- | --- | --- | --- | --- | --- |
| | | | 1 atm. | 5 atm. | 10 atm. |
| Pure Tin | 2.51 × 10⁶ | 17.93 | 0.026 | 0.13 | 0.26 |
| Tin/Iron (50:50 by weight) | 0.625 × 10⁶ | 24.41 | 0.141 | 0.70 | 1.41 |

It is evident from the data in Tables 1 and 2 that pure tin systems require substantially more steam to produce hydrogen than the dissolved iron systems in accordance with the present invention. Table 2 also shows that the nominal residence time available for tin to react with the steam is considerably less than the nominal residence time available for iron dissolved in tin to react with the steam. Nominal or apparent residence time is the time available for the steam (reactant of the process) to traverse the space occupied by the quantity of reactive metal employed. In Table 2, the melt volume is the quantity of metal required by stoichiometry at the hydrogen production rate of 4.439 tons of hydrogen per hour. During this time, ideally, hydrogen will be produced in an amount corresponding to the thermodynamic $pH_2/pH_2O$ ratio. An amount of reactive metal greater than the stoichiometric amount may be used to increase nominal residence time, but the consequence is increased reactor size and cost. Increased pressure also increases the reaction time available between the steam and the reactive metal, however, this also adds to cost.

Thus, one significant advantage of utilizing a reactive metal dissolved in a diluent metal in accordance with the present invention is that the residence time of the steam within the reactor is increased with respect to the mass of the reactive metal. That is, a given mass of iron will occupy a first volume as pure iron, but the same mass of iron will be distributed over about twice the volume if the iron is in a 50 weight percent mixture with a diluent metal such as tin.

FIG. 1 illustrates a phase diagram for iron and tin adapted from Hari Kumar, K. C., et al., *Calphad*, 20, 2, 139–149 (1996). It can be seen from FIG. 1 that one effect of adding iron (the reactive metal) to tin (the diluent metal) is to substantially lower the melting temperature of the iron. The liquidus of the metal mixture decreases from 1538° C. (pure iron) to about 1134° C. at a melt composition of about 48.7 weight percent tin and 51.3 weight percent iron.

According to one embodiment, it is preferred that the metal mixture be maintained at a temperature above the liquidus line AC of FIG. 1 (e.g., above 1134° C.). A metal-steam reaction temperature that is too high, however, adds significantly to the operating costs. For the completely molten iron/tin system illustrated in FIG. 1, the melt should be maintained at a temperature above the liquidus temperature of about 1134° C., more preferably at a temperature of at least about 1200° C. For the purpose of reasonable economics, the temperature should not be greater than about 1500° C. and more preferably is not greater than about 1400° C. A particularly preferred temperature range for the completely molten tin/iron metal mixture is from about 1200° C. to 1300° C. At 1200° C., about 50 weight percent iron dissolves in tin with sufficient superheat and the mixture stays in the molten state as iron is oxidized. Also, the reaction between steam and liquid iron dissolved in tin to form pure hydrogen at 1200° C. is also quite vigorous and the reaction kinetics are excellent. Furthermore, the thermodynamics for the steam/iron system at 1200° C. are relatively good, requiring an excess of only about 12.2 tons of steam to produce each ton of hydrogen (1.37 moles of steam per mole of hydrogen).

According to this embodiment, it is preferred that that the metal mixture initially include at least about 3 weight percent iron in the molten metal mixture, more preferably at least about 10 weight percent iron, even more preferably at least about 20 weight percent iron and even more preferably at least about 50 weight percent iron in the molten metal mixture. Further, the amount of iron in the molten metal mixture should preferably not exceed about 85 weight percent and more preferably should not exceed about 80 weight percent. The balance of the metal mixture in a preferred embodiment consists essentially of tin. Accordingly, the amount of tin in the system is preferably not greater than about 97 weight percent, more preferably is not greater than about 90 weight percent and even more preferably is not greater than about 80 weight percent. The molten metal mixture preferably includes at least about 15 weight percent tin and more preferably at least about 20 weight percent tin.

Although the present invention requires the presence of a molten metal mixture, according to one embodiment, insoluble phases such as in the form of particles can be dispersed within the molten metal mixture. This assembly of a molten metal mixture and insoluble phase is termed a slurry. According to one embodiment, the steam is contacted with a slurry that includes a molten metal mixture and a solid second phase, wherein the solid second phase includes reactive metal-containing particles and is adapted to supply additional reactive metal to the molten metal mixture. Preferably, the particles are metallic particles (e.g, not oxide particles). For example, the slurry could include iron-rich metallic particles within an iron/tin melt that is saturated with iron. As the steam reduction process proceeds, dissolved iron is removed from the molten metal mixture by oxidation of the iron and additional iron from the iron-rich particles dissolves in the molten metal to keep the molten metal portion of the slurry saturated with iron.

Referring to the phase diagram in FIG. 1, the composition within the two-phase region defined by point A (83.3 wt. % Fe at 1134° C.), point B (84 wt. % Fe at 1134° C.), point C (12 wt. % Fe at 895° C.) and point D (3 wt. % Fe at 895° C.) includes an iron/tin melt with about 3 wt. % to 84 wt. % total iron, with a portion of the iron as iron-rich metallic particles dispersed in the melt. At a given temperature between about 895° C. and about 1134° C., as iron is removed from the molten metal due to iron oxidation, additional solid iron from iron-rich particles will dissolve, thereby maintaining the level of iron in the melt at bulk saturation until the solid iron is depleted. This replacement of iron that is lost to oxidation by iron originating from the iron-rich particles keeps the activity of the iron high, which, in turn, maximizes the production of hydrogen. For example, at a temperature of about 950° C. and about 50 wt. % total iron, the molten metal mixture will include about 4 wt. % dissolved iron in the system. As the dissolved iron is oxidized, additional iron metal from the iron-rich particles will dissolve to maintain 4 wt. % dissolved iron in the melt. The activity of the iron, therefore, remains unchanged as a consequence of dissolution of iron-rich particles.

Thus, according to this embodiment, the slurry, comprised of the molten metal mixture and iron-containing particles, is maintained at a temperature below the liquidus temperature of 1134° C. and is at least about 895° C., more preferably from about 900° C. to about 1134° C.

One advantage of such a method is that the activity of the iron remains constant and in fact is close to one, and therefore the production rate of hydrogen remains constant and maximized throughout the steam reduction process.

The desired effect of constant activity of the reactive metal would also be observed if the process were carried out within the miscibility gap region of FIG. 1; however, the activity of iron would be somewhat less than one.

A thermodynamic relationship exists between the partial pressure of hydrogen in the off-gas, the reaction temperature and the weight percent iron in the molten metal composition. The thermodynamic quantity, referred to as the "activity" of iron, varies as a function of iron concentration and strongly influences the ratio of hydrogen to water in the off-gas. The production of hydrogen is maximized by operating within phase regions that establish a high iron activity over a wide composition range through the use of a second phase in equilibrium with the reacting phase. This applies both to the liquid—liquid region, above the line AC in FIG. 1, as well as the solid-liquid region, below the line AC and to the right of the line AB. However, the present invention does not exclude operation in the iron-rich liquid phase.

Figure 2:
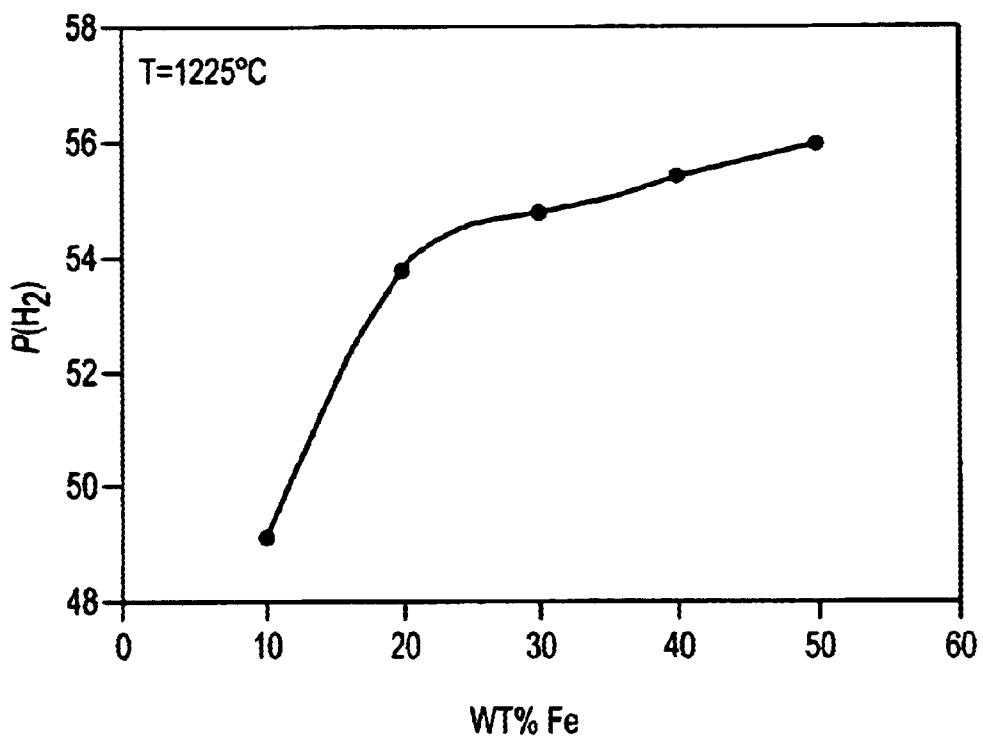
FIG. 2 illustrates the production rate of hydrogen as a function of iron content in the reactor according to an embodiment of the present invention.
Figure 3:
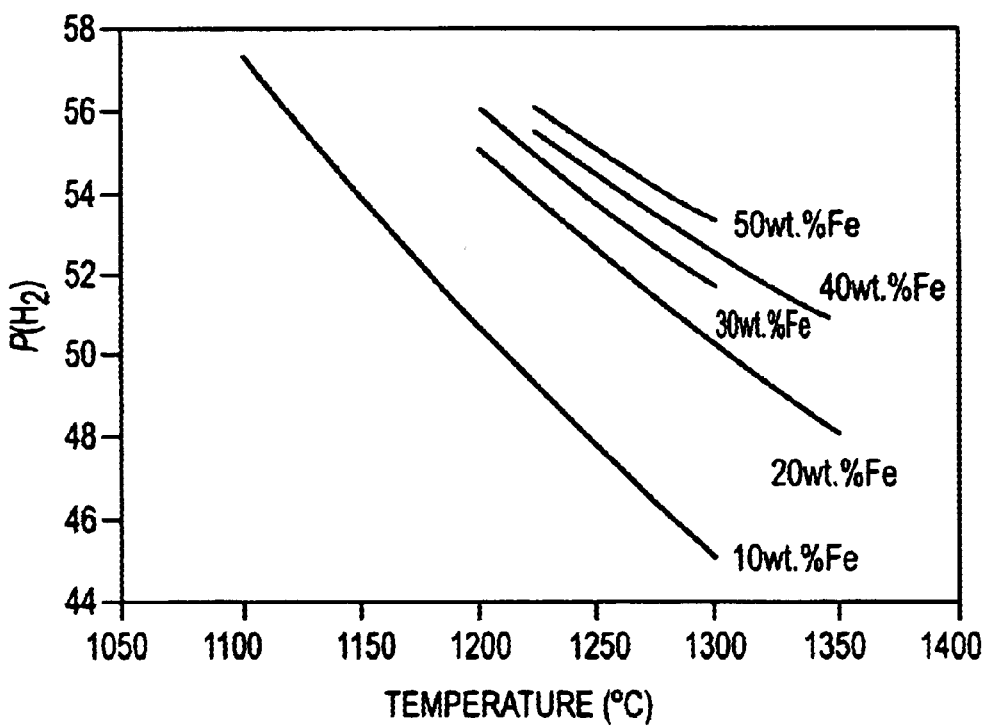
FIG. 3 illustrates the production rate of hydrogen as a function of iron content and reaction temperature according to an embodiment of the present invention.

FIG. 2 illustrates the relationship between the level of hydrogen in the off-gas as a function of iron content in the molten metal mixture. FIG. 2 was calculated based on thermodynamics of the reaction at 1225° C. It is evident that the hydrogen production rate rapidly decreases as the iron content drops from 20 weight percent to 10 weight percent. FIG. 3 illustrates the hydrogen production as a function of temperature and iron content.

At levels below about 20 weight percent iron and temperatures above about 1134° C., the production capacity for hydrogen is impaired since: (1) the $pH_2/pH_2O$ drops significantly; and (2) only short periods of time are available before gas flows (i.e., steam and metal oxide reductant) have to be switched.

Thus, steam is contacted with the molten metal mixture to generate hydrogen and to convert the reactive metal to a metal oxide. The steam is contacted with the molten metal mixture in a manner that promotes good mixing and contact with the molten metal mixture. For example, the steam can be contacted with the molten metal mixture by injection through a top-submerged lance or through a porous ceramic diffuser disposed at the bottom of a reactor. Preferred reactor systems in this regard are discussed below. The reactor temperature can be controlled to maintain a substantially constant temperature by controlling the incoming steam temperature and quantity and/or by adding oxygen to the reactor.

The steam reduction reactor can be maintained at an elevated pressure if necessary for adequate residence time in the reactor, as is discussed above. For example, it may be desirable to maintain an elevated pressure, such as at least about 15.3 atmospheres (225 psi). A slightly elevated pressure can also be beneficial for providing a hydrogen gas stream with sufficient pressure for transmission (e.g., a line pressure of about 200 psi). However, significantly increased pressure adds to capital cost and therefore the pressure in the steam reduction reactor is preferably not greater than about 600 psi and more preferably is not greater than about 225 psi.

According to the present invention, a slag layer is maintained over the molten metal mixture. A slag layer provides a number of advantages, including preventing the iron oxide from exiting the reactor. The temperature in the steam reduction reactor should be sufficient to maintain the slag layer that forms over the metal mixture in the molten state over a range of compositions. As the reactive metal is oxidized, a decrease will occur in the concentration of the reactive metal in the metal mixture and the metal mixture should remain molten as the reactive metal is oxidized. Similar to the range of compositions for the molten metal discussed previously with respect to FIG. 1, the range of preferred slag compositions required to ensure adequate slag fluidity and reactivity, and prevent foaming can be adjusted, as necessary, for a given temperature. For example, fluxes can be added to the reactor to adjust the properties of the slag. One flux system is indicated by the liquid surface of $SiO_2$, FeO, CaO, MgO, $Na_2O$ and $K_2O$. However, sulfur and other cations may be incorporated in this or other slags to secure satisfactory slag chemistry.

The metal oxide (e.g., wüstite and/or magnetite) that is generated by the steam reduction can advantageously be trapped (dissolved or suspended) in the slag layer within the reactor. At the preferred temperatures, the iron oxide is incorporated into the slag, which is lighter than the metal mixture. Therefore, as the dissolved iron is depleted from the molten metal mixture, the iron oxide rises through the molten metal and contributes to the slag layer on top of the molten metal. It is an advantage of this embodiment of the present invention that the oxide formed upon reaction of the reactive metal with the steam has a density that is less than the density of the molten metal mixture, whereby the oxide rises to the slag layer. Preferably, the metal oxide is at least about 10 percent less dense than the molten metal mixture. This also enables the metal to sink from the slag layer to the molten metal mixture upon reduction of the metal oxide. As is discussed above, this accumulation of iron oxide in the slag may require the addition of a flux such as $SiO_2$, FeO, CaO, MgO, $Na_2O$, $K_2O$ or mixtures thereof to maintain the slag in the preferred condition with respect to viscosity, reactivity, foaming, and the like.

The molten metal mixture must be contained within a suitable reactor to maintain suitable reaction conditions. Further, the reactants should be provided in a manner conducive to good mixing and high contact surface area. High-temperature reactors suitable for establishing good gas/liquid contact are utilized in the chemical, and especially metallurgical industries.

A preferred reactor system according to the present invention utilizes a top-submerged lance to inject the steam into the molten metal. Such reactors have been used in the commercial production of tin from tin ore (cassiterite). Examples of reactors utilizing a top-submerged lance to inject reactants are disclosed in U.S. Pat. Nos. 3,905,807, 4,251,271, 5,251,879 by Floyd, U.S. Pat. No. 5,282,881 by Baldock et al., U.S. Pat. Nos. 5,308,043 and 6,066,771 by Floyd et al. Each of these U.S. patents is incorporated herein by reference in their entirety. Such reactors are capable of injecting reactants (e.g., steam) into the molten metal at extremely high velocities, approaching Mach 1, thereby promoting good mixing of the reactants.

Figure 4:
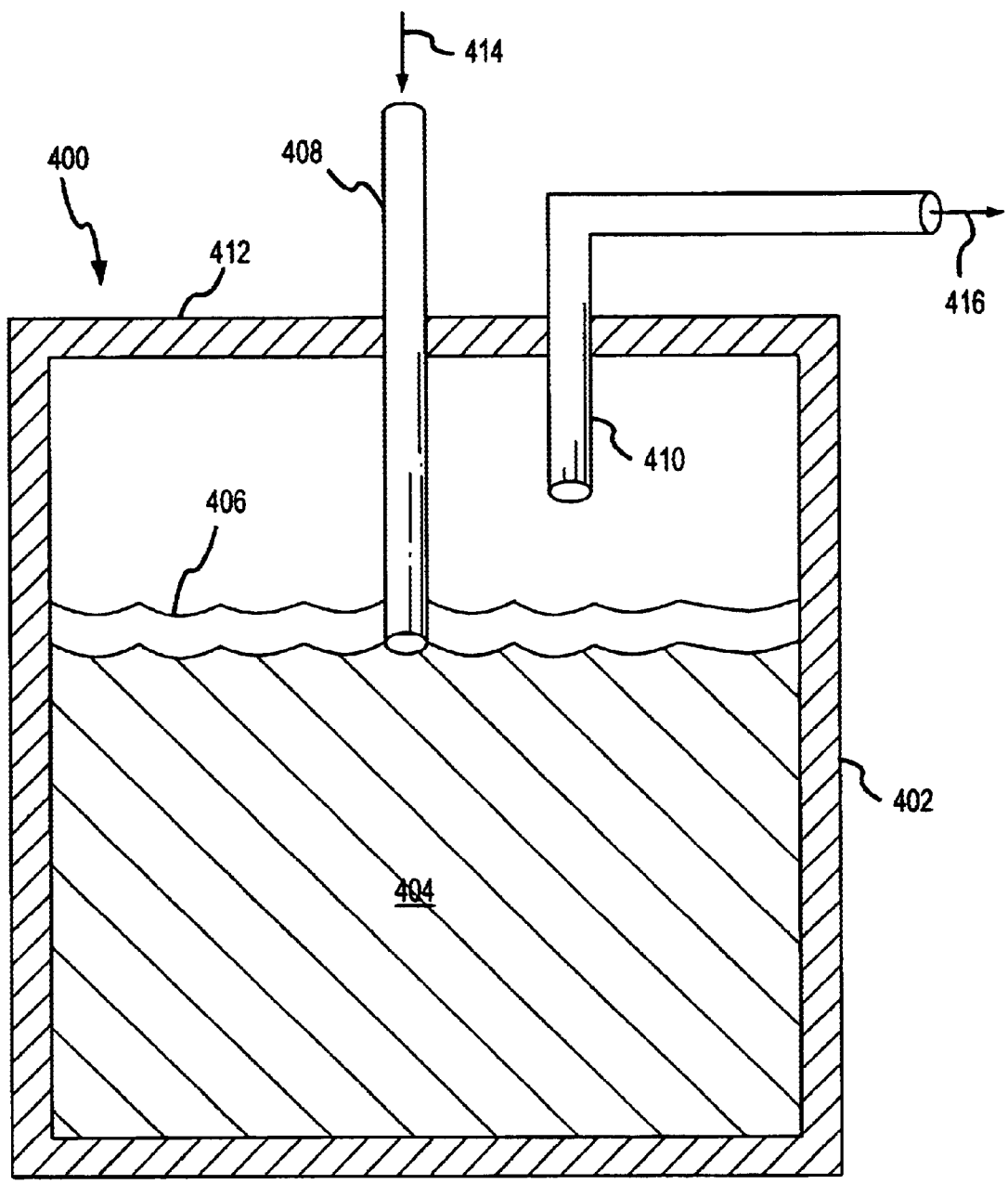
FIG. 4 illustrates a reactor operating in steam reduction mode according to an embodiment of the present invention.

A reactor incorporating a lance for injection of steam is illustrated in FIG. 4. The reactor 400 includes refractory sidewalls 402 that are adapted to contain the molten metal mixture 404. Heating means (not illustrated) can be provided, if necessary, to maintain the temperature within the reactor 400. A top-submerged lance 408 is disposed through the reactor top wall 412 and is adapted to inject steam into the metal mixture 404 at a high velocity. Preferably, the top-submerged lance 408 terminates and injects steam below the surface of the slag layer 406 and near the interface of the molten metal mixture 404 and the slag layer 406. As steam is introduced through the lance 408, iron from the metal mixture 404 oxidizes to iron oxide. The iron oxide rises and accumulates in a slag layer 406. A gas product 416 including hydrogen gas co-mingled with steam is extracted from outlet port 410, after which the excess steam can be condensed to form a substantially pure hydrogen gas stream.

The steam reduction process is continued until the rate of hydrogen production decreases to a sufficiently low level. Thereafter, a reductant is introduced into the reactor containing the molten metal mixture and the slag to reduce the iron oxide back to the metal. The point at which the steam reduction process is terminated and the metal oxide reduction process is begun can readily be determined based on economic considerations. That is, at some point the hydrogen production rate in the steam reduction reactor will decrease to a point that is economically advantageous to terminate the steam reduction and begin regeneration of the metal from the metal oxide.

In this regeneration step, which can be viewed as reductive cleaning of the slag, the iron oxide in the slag is reduced and returned to the melt as iron. This is achieved by lowering the oxidation potential of the system by introducing a reductant to the reactor. The reductant lowers the oxidation potential of the system thereby driving the iron back into the melt. The reductant can be carbon monoxide, coal and/or other carbon source. According to a preferred embodiment, the oxidation potential of the system is lowered by injecting particulate carbon, hydrocarbon or liquid hydrocarbon into the slag with an oxygen-containing gas under conditions of intense mixing. The particulate carbon or hydrocarbon can include coke, coal or other organic material. A liquid hydrocarbon, such as #6 or other oil can also be used. Waste materials such as scrap tires can also be used. Scrap tires can advantageously supply additional iron to the reactor to make up for incidental losses of the iron.

A top-submerged lance is preferred for introducing the air or other oxygen-containing gas into the reactor in a manner that insures good mixing. Prior to injection of a reducing composition, the reactor may be purged, such as with steam, to remove any hydrogen from the reactor. After the reductive cleaning of the slag is complete, the reactor may again be purged, with air or steam, for the purpose of removing any carbon that may be dissolved in the iron and/or for the purpose of removing any other tramp elements that may be in either the melt or slag, that otherwise would contaminate the hydrogen produced when steam is re-introduced into the reactor.

In a preferred embodiment according to the present invention, a reductant derived from a carbon source such as coal and an oxygen source such as air or oxygen-enriched air is injected into the molten metal mixture and slag layer. The coal can be injected through the top-submerged lance with the air, or can be added separately. It is an advantage to use coal as the reductant source, because, compared to oil and gas, it is both abundant and relatively inexpensive. Coal can also supply iron to the reactor to make-up for iron that is lost during processing. Scrap tires and other waste materials can also supply some iron. The metal oxide reduction process is continued until a sufficient amount of iron metal has been re-dissolved in the molten metal mixture.

Preferably, the reaction conditions when operating in the mode to reduce the metal oxide to metal are substantially identical to the conditions during steam reduction. That is, it is preferred that the temperature and pressure of the metal oxide reduction reactor are the same or very similar to the temperature and pressure of the steam reduction reactor. Thus, the temperature is preferably at least above the liquidus (e.g., about 1134° C. for the tin/iron system) and more preferably is at least about 1200° C. Preferably, the temperature does not exceed about 1400° C. and more preferably does not exceed about 1300° C. In a particularly preferred embodiment, the temperature is about 1200° C. in both reactors and the pressure is slightly above atmospheric pressure in the steam-reduction reactor and slightly below atmospheric pressure in the metal oxide reduction reactor.

Figure 5:
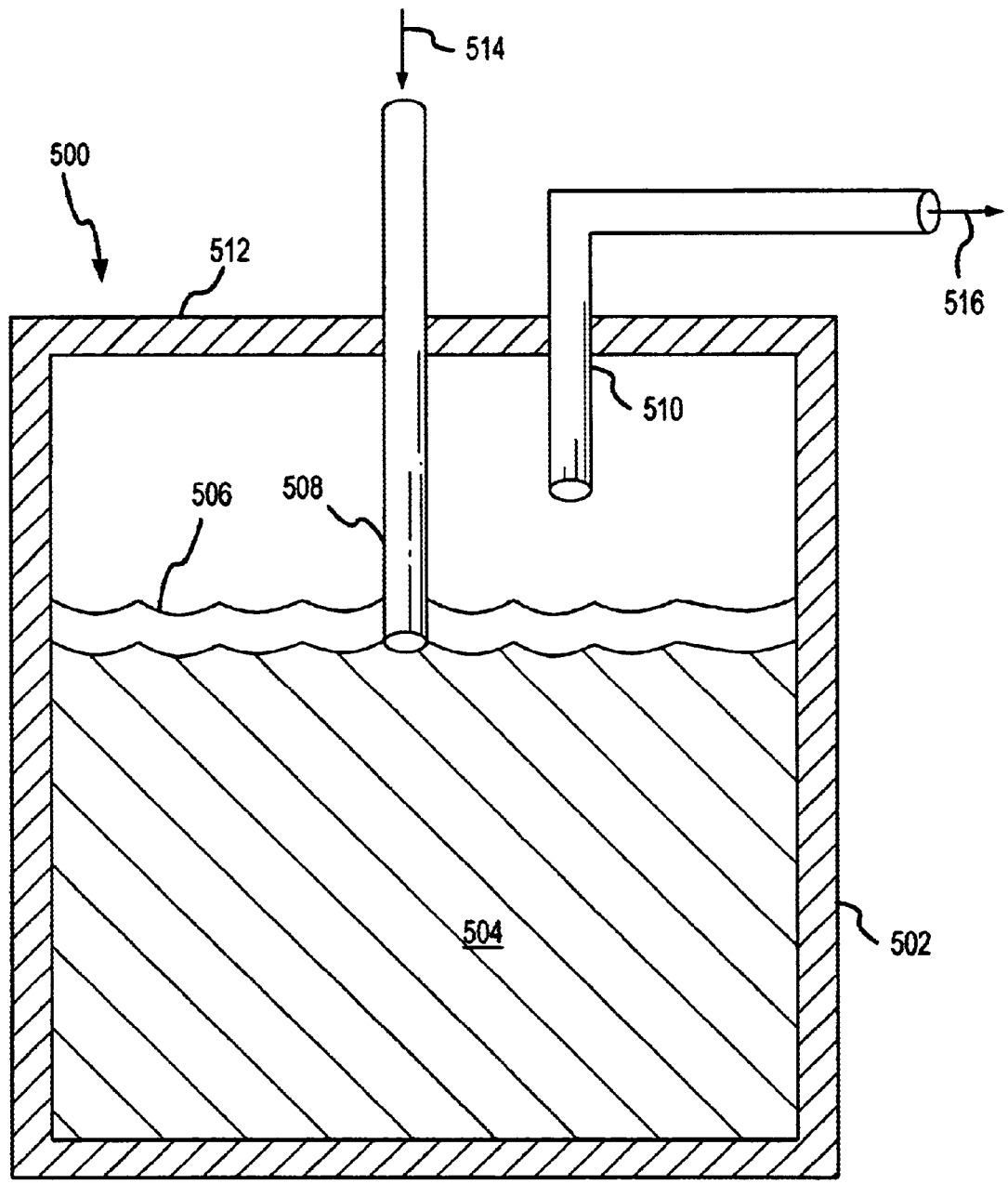
FIG. 5 illustrates a reactor operating in metal oxide reduction mode according to an embodiment of the present invention.

Referring now to FIG. 5, a reactor 500 operating in metal oxide reduction mode is illustrated. Preferably, the reactor is physically identical to the steam reduction reactor illustrated in FIG. 4, and includes insulated side-walls 502. The metal mixture 504 initially includes predominantly tin, although some iron will still be present. The slag layer 506 includes the iron oxide that was formed during the steam reduction process described above. Carbon 514, such as in the form of coal, can be injected through the lance 508 that is disposed through the reactor top wall 512, along with an oxygen source such as oxygen-enriched air. Alternatively, carbon can be added to the reactor separately and the gaseous oxygen source can be injected through the lance. Under the reducing conditions maintained in the metal oxide reduction reactor by the addition of carbon and oxygen, the iron oxide is reduced back to iron, which then re-dissolves within the molten metal mixture 504. Off-gases 516 such as carbon dioxide and nitrogen can be removed through outlet port 510.

In the metal oxide reduction step, ash formed from coal will also be incorporated into the slag. The slag, which can be pozzolanic when CaO is added as a flux, can be periodically or continuously withdrawn, ground and can be used as a replacement for Portland cement. Alternatively, the slag may be partially granulated by quenching with water. The granulated slag can then be drained and disposed to waste. Impurities in the coal (for example sulfur, chlorine and fluorine) that are converted during combustion to gaseous species (such as sulfur dioxide, hydrogen chloride and hydrogen fluoride) can be removed by wet scrubbing. Alternatively, the sulfur can be converted into ammonium sulfate, which is useful as a fertilizer compound, and the remaining impurities reacted to render them solid so that they can be directed to waste. Carbon dioxide and nitrogen from the air and fuel are the only gaseous effluents from the metal oxide reduction process.

Controlling the oxidation potential of the slag controls the amount of iron oxide in the slag that is reduced to iron that subsequently reports to the melt during metal oxide reduction. This can be achieved by controlling the relative amount of coal (or other carbonaceous fuel) and oxygen that is injected into the slag system. Some iron oxide will be dissolved in the slag, the amount determined by the slag chemistry. Another portion of the iron oxide may be present in the slag as slurried particulate solids if the slag is saturated in iron oxide.

In accordance with the foregoing, it is apparent that two or more reactors can be operated in parallel for the production of hydrogen in a continuous manner. As iron is depleted from the molten metal mixture in the steam reduction reactor, and as the iron oxide is reduced to metal in the metal oxide reduction reactor, their functions can be reversed by switching the flows into and out of the reactors. Although the functionality of the reactors is reversed, there is no movement of metal or metal oxide into or out of the reactors. This has a significant and favorable impact on cost. The reactors can utilize a single top-submerged lance for the injection of steam or the injection of carbon and oxygen to form carbon monoxide. Alternatively, a reactor with two lances (one for steam and another for carbon/oxygen) can be utilized. Additional ports for the injection of steam can also be provided, such as on the sides of the reactor.

Figure 6:
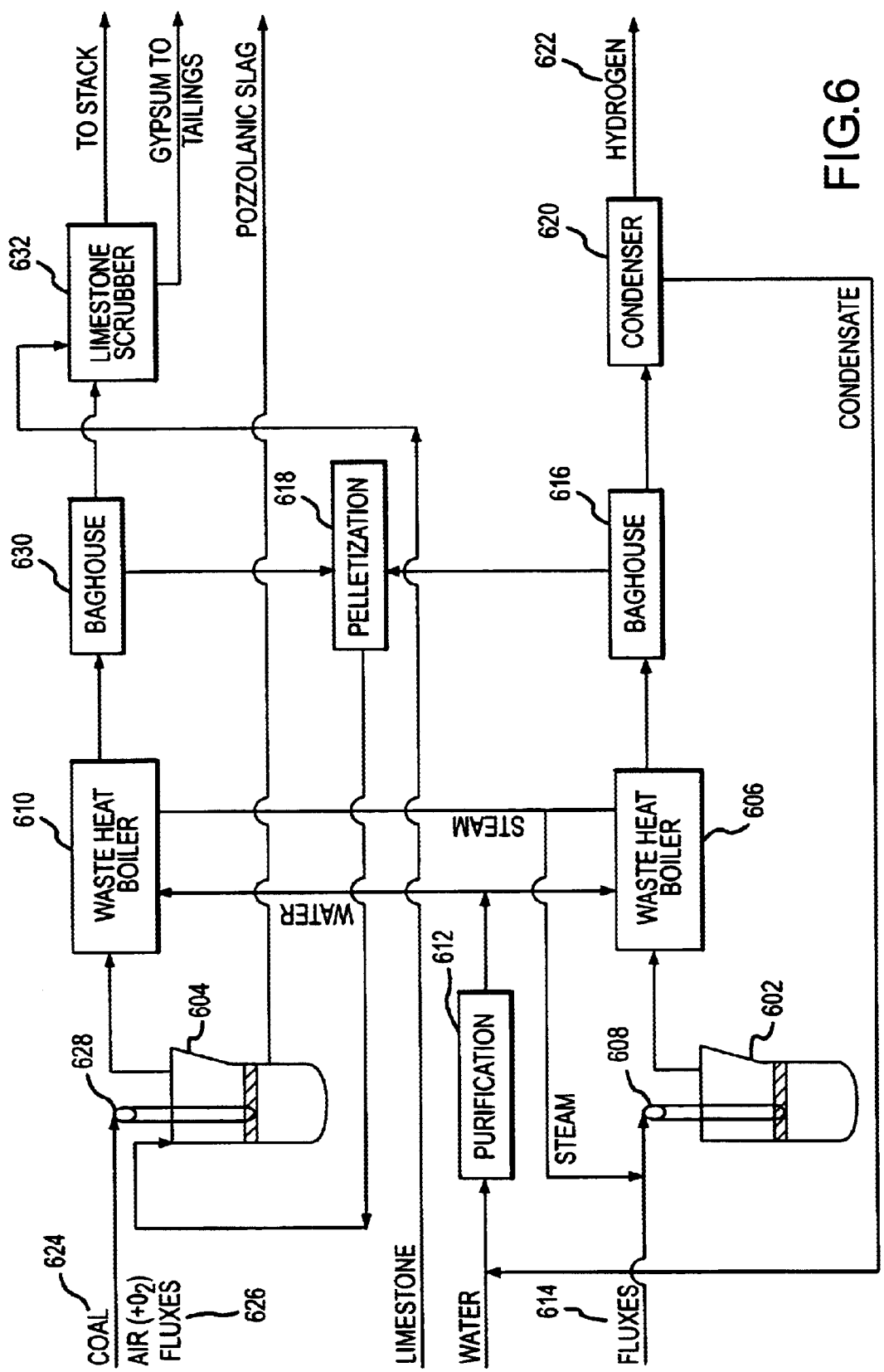
FIG. 6 illustrates a process flow for continuous hydrogen production according to the present invention.

A flowsheet illustrating the continuous generation of hydrogen using two reactors in accordance with the present invention is illustrated in FIG. 6.

The hydrogen generation process employs two reactors 602 and 604 wherein one of the reactors operates in steam reduction mode while the other operates in metal oxide reduction mode. As illustrated in FIG. 6, reactor 602 is operating in steam reduction mode and generates hydrogen and reactor 604 is operating in metal oxide reduction mode.

Steam is provided by heating water in waste heat boilers 606 and 610. Prior to heating in the boilers, the water should be subjected to purification 612 such as by using reverse osmosis and de-ionization to remove contaminants that can affect boiler operation or introduce impurities into the hydrogen product gas. Steam is produced in the boilers and is provided to the reactor 602 at a super-heated temperature that is sufficient to maintain isothermal conditions within the steam reduction reactor 602 at the operating temperature, e.g., about 1200° C.

The steam is injected into the reactor 602 through a through a top-submerged lance 608. The top-submerged lance provides good mixing and a high contact surface area between the steam and the molten metal mixture to promote the steam reduction/metal oxidation reaction. The reactor 602 is sealed to prevent egress of hydrogen and steam from the reactor. Also, the reactor may be placed under modest pressure to provide a sufficient contact time for the steam and to deliver the hydrogen under pressure.

Other materials can be added to the reactor if necessary. For example, fluxes 614 can be added to control the properties of the slag layer that forms above the molten metal mixture as the steam reduction reaction oxidizes the metal. Possible fluxes include $SiO_2$, FeO, CaO, MgO, $Na_2O$ or $K_2O$. Additionally, other materials such as tin compounds, cassiterite ore or other materials such as iron compounds or ore may be added to make-up for losses of metal values. According to a particularly preferred embodiment, cassiterite ore ($SnO_2$) is injected into the reactor to make-up for tin losses.

A hydrogen-containing gas that includes hydrogen and excess steam is removed from the reactor 602. The hydrogen-containing gas can be passed through the waste heat boiler 606 to provide heat for additional steam, thereby conserving heat values. The hydrogen-containing gas stream gas can also include some contaminants, such as the sub-oxide of tin oxide (SnO), the hydrated sub-oxide of tin ($SnO_2H_2$), and entrained particulates of (frozen) slag which volatilize or are ejected from the molten metal bath and slag, and such contaminants can be removed in a baghouse 616. For example, the volatile tin compounds can be condensed from the gas stream and, along with particulate slag, captured either in the waste heat boiler or in the baghouse. After being captured, these materials can be pelletized 618 and optionally provided to either reactor 602 operating in steam reduction mode or reactor 604 operating in the metal oxide reduction mode for recovery of metal values and control of the slag chemistry. After removal of contaminants, if any, the hydrogen gas stream is treated in a condenser 620 and/or chiller (not shown) to condense the excess steam from the hydrogen gas stream and form a high purity hydrogen gas stream 622. Water condensed from the hydrogen gas stream can be recycled for additional steam production.

Simultaneously, metal oxides are reduced in reactor 604. The metal oxides are reduced by a reductant such as CO, which can be formed by injecting coal 624 (or other carbonaceous material) and oxygen 626 through a top-submerged lance 628. As with reactor 602, the top-submerged lance 628 provides good mixing and contact surface area between the reactants. The oxygen-containing gas should also be injected using a top-submerged lance or similar device. It is possible to add the particulate coal to the reactor 604 by other means, such as by simply dropping the coal into the reactor.

The ash-forming minerals that are typically part of the coal (or other carbonaceous material) employed along with oxygen to bring about the reduction of the reactive metal oxides, contribute to the slag layer within the reactor 604. When coal 624 is used and there is adequate calcium oxide (CaO) in the slag, the slag layer can be a salable pozzolanic by-product. As with reactor 602, other materials such as fluxes can be injected into the reactor 604, for example to control the properties of the slag such as slag fluidity or tendency to foam.

The off-gas from the metal oxide reduction reactor 604 can include carbon dioxide, nitrogen and some contaminants from the coal such as sulfur. Heat from the off-gas can be conserved in the waste heat boiler 610 where steam is generated. The gas stream can then be treated in a bag-house 630 to remove particulate contaminants. The remaining gases can be treated in a limestone scrubber 632 to form environmentally benign stack gases and gypsum from the sulfur that originates from the coal. Alternatively, the sulfur can be treated with anhydrous ammonia to form ammonium sulfate, a useful compound for fertilizing soil.

Thus, as iron is depleted from the molten metal mixture in the steam reduction reactor 602, and as the iron oxide is reduced to metal in the metal oxide reduction reactor 604, their functions can be reversed by switching the flows into and out of the reactors. Prior to switching gas flows, the reactors can be purged to remove residual gases and contaminates, if any. Accordingly, hydrogen gas can be produced in a substantially continuous manner.

The hydrogen gas that is produced according to the present invention preferably can have a high purity. Preferably, the gas stream includes at least about 30 volume percent hydrogen with the remainder composed primarily of water in the form of steam. Preferably, the purity of the hydrogen is greater than about 99% or more preferably greater than about 99.9% after removal of the residual water in a condenser. It is an advantage of the present invention that the hydrogen gas does not require separation from other gas species such as carbon monoxide and carbon dioxide as is the case for hydrogen produced by either steam reformation of methane or coal gasification, which two methods cover the bulk of hydrogen currently produced. In the event that carbon species (e.g., CO) are initially present in the gas stream due to dissolved carbon in the molten mixture, the gas can be extracted and burned for fuel value until the hydrogen purity reaches a sufficient level. That is, any dissolved carbon will preferentially react with the steam to form CO before large amounts of hydrogen are produced by oxidation of the reactive metal. Further, the method and apparatus of the present invention enable the production of high volumes of pure hydrogen gas at a low cost. Hydrogen gas has a fuel value of about 51,623 BTU/lb and is useful as a component of a combustion gas. Hydrogen can also be used for hydrogenation processes and in semiconductor fabrication. Further, hydrogen is used directly as a fuel in a fuel cell, such as a proton exchange membrane fuel cell (PEMFC).

One aspect of the present invention is directed to the treatment of coal to produce energy value from the coal while minimizing the discharge into the atmosphere of harmful by-products that are typically associated with the conversion of coal to energy. The method enables the extraction of the available energy content from the coal in the form of a medium BTU gas while reducing the atmospheric discharge of harmful by-products.

Coal exists in relative abundance in the United States and many other regions, including third-world regions with under-developed energy production infrastructure. One of the problems associated with the use of coal is that the coal must typically be cleaned or purged of its mineral matter content, including sulfur; notwithstanding, there usually is an additional need for post-combustion gas scrubbing to meet environmental standards.

It is an advantage of the present invention that the coal feedstock can include low-grade coal including high-sulfur coal and other low-grade coals. Such low-grade coals are readily available and are available at low cost. As used herein, the term low-grade coal refers to coal having a sulfur content in excess of 2 weight percent and an ash content in excess of about 10 weight percent.

Generally, the method of the present invention includes providing the coal feedstock to a hydrogenation unit and contacting the coal feedstock with a treatment gas that includes $H_2$ produced in accordance with the foregoing. The hydrocarbons in the coal that are volatile will react with hydrogen to form methane ($CH_4$). The exit gases from the hydrogenation unit can be scrubbed if necessary to produce a clean, high BTU gas product. A portion of this gas product can be burned in a combined cycle generator taking advantage of the generator's high thermal-to-electric conversion efficiency. Another portion of the gas product can be combusted in a conventional boiler with the non-volatile carbon that is formed in the hydrogenation unit. The carbon will be essentially free of sulfur because the hydrogen treatment gas is a strong desulfurizing agent. In one embodiment, another portion of the carbon that is produced in the hydrogenation unit can be recycled back to the metal oxide reduction step where the metal oxide is reduced back to the reactive metal. Thus, the coal is advantageously partitioned into the volatiles (treated with hydrogen) and fixed carbon (reacted with oxygen).

Figure 7:
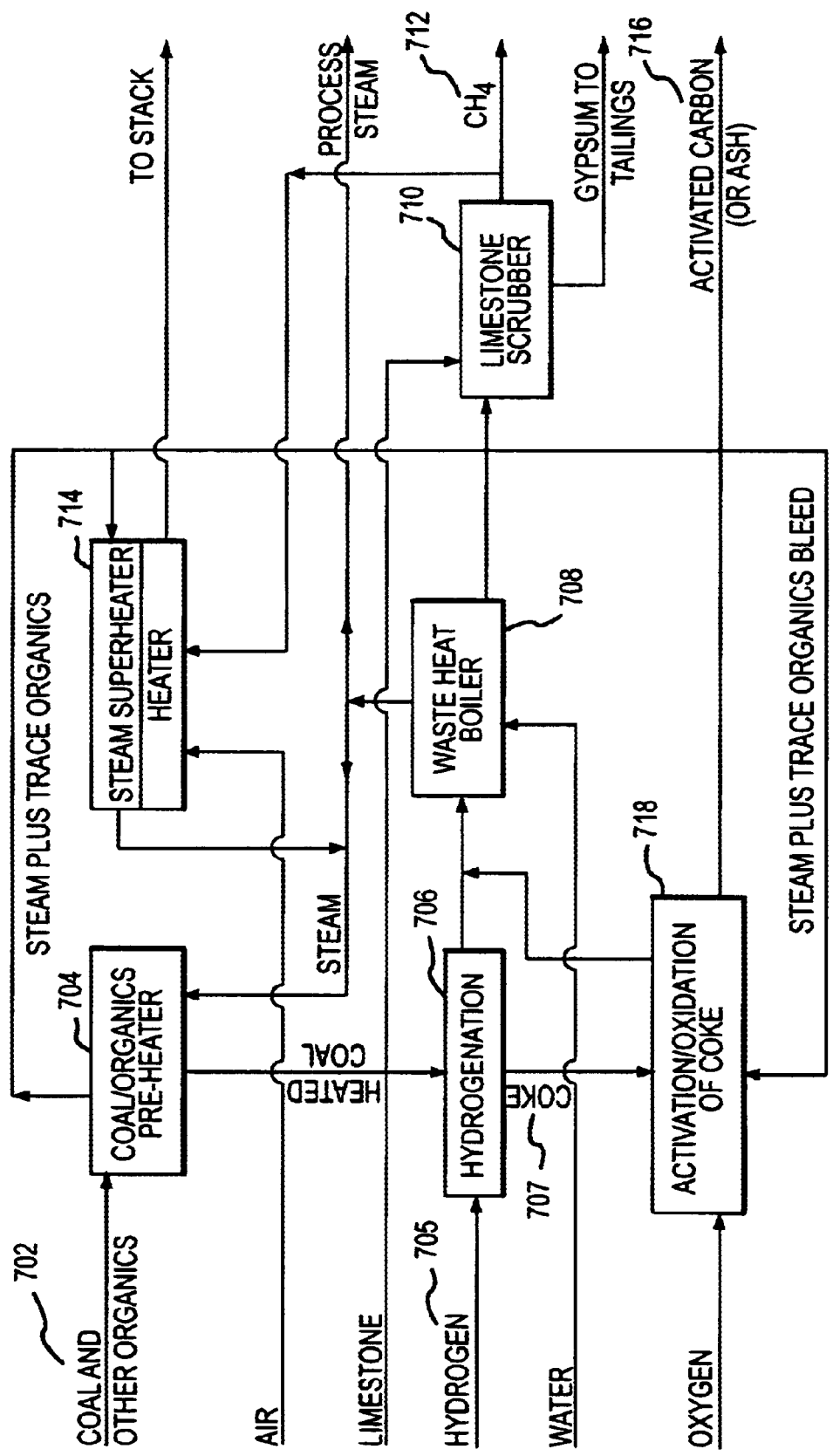
FIG. 7 illustrates a process flow for the treatment of coal or other organic-containing feed material according to the present invention.

Referring to FIG. 7, coal 702, optionally with other organics, is first conveyed to a pre-heater 704 where the temperature of the coal is raised. The heated coal is then conveyed to a hydrogenation unit 706 where the coal is contacted with hydrogen gas 705 that has been formed in accordance with the method described above.

The hydrogenation unit 706 can be a fluidized bed reactor or other reactor that is suitable for the treatment of particulate coal. The unit is preferably operated at ambient or near ambient pressure, such as a pressure of not greater than about 5 psi.

It is a cost advantage of the present invention that the hydrogenation unit 706 is not operated at a substantial elevated pressure. Grossly elevated pressures do produce additional methane, a gas with a very high BTU content. For the purpose of converting coal to clean energy, however, it is more cost effective to produce the combustible gases carbon monoxide and hydrogen from the coke, a residue from the hydrogenation step. Gases derived from the reaction between coke and steam (CO & $H_2$) are combined with the methane from hydrogenation to produce a valuable medium BTU gas. The reaction in the hydrogenation unit 706 is preferably carried out at a temperature of at least about 700° C. and preferably not greater than about 1100° C., such as from about 800° C. to about 900° C. The reaction that occurs in the hydrogenation unit is exothermic and therefore the need for the addition of external heat is minimal.

Coal is a complex mixture of chemical compounds that are primarily organic compounds. While coal is predominately a hydrocarbon, impurities such as sulfur and nitrogen are trapped in the coal. These impurities, released as the coal is combusted, lead to the formation of sulfuric acid and nitric acid if released into atmosphere and must be scrubbed from the off-gas in a typical coal-based power plant. Further, when the coal is burned, the carbon combines with oxygen from the atmosphere and forms $CO_2$, a well-known greenhouse gas that traps the earth's heat.

According to the present invention, when the coal 702 is treated in the hydrogenation unit 706 with the hydrogen treatment gas 705, the coal is not burned. Rather, it is heated to remove the volatile components in the coal. These volatile components advantageously form a high BTU product gas comprised largely of methane. The residue from the removal of the volatiles is purified by the action of the hydrogen, including removal of sulfur and nitrogen, and the resulting purified carbon (i.e., coke 707) can: (a) be combusted in a conventional boiler with methane and without excessive formation of detrimental by-products; (b) be converted to carbon monoxide and hydrogen which gases are added to the methane from the hydrogenation reactor 706 to produce a medium BTU gas for combustion; (c) be activated by oxygen and steam to form an activated carbon 716; or (d) some combination of the above.

The methane-containing gas stream that is produced by the hydrogenation reaction can be passed through a waste heat boiler 708 to conserve heat value from the gas stream. Thereafter, a limestone, lime or ammonia scrubber 710 can be used to remove contaminants from the methane-containing gas stream such as sulfur, thereby producing a high purity methane-containing gas 712. Sulfur in the coal will form hydrogen sulfide ($H_2S$) that can be scrubbed from the methane gas stream. It is advantageous to scrub the methane gas stream prior to combustion, if any, since combustion creates a higher volume gas stream.

The methane gas can be combusted on-site to generate electricity, or can be treated to remove CO (if any) and provided to end-users as a pipeline gas. Further, a portion of the $CH_4$ can be cycled back to the other unit operations to provide process heat. For example, a portion of the $CH_4$ can be diverted to the steam superheater 714.

The hydrogenation treatment advantageously removes the impurities in the coal 702 forming a clean coke product 707. The coke product 707 can be treated in an activation/oxidation unit 718 if necessary, to form: (a) clean activated carbon 716, (b) a clean coke (c) a mixed gas comprised of hydrogen and carbon monoxide or (d) some combination of the foregoing.

According to one embodiment of the present invention, a portion of the coke 707 can be cycled back to the metal oxide reduction reactor (FIG. 5) for the reduction of the metal oxide. The carbon will be converted to CO and the ash incorporated into the slag that can be withdrawn periodically. The remaining coke from the hydrogenation unit 706 can be burned in a conventional boiler with methane for additional energy production.

Further, a portion of the hydrogen gas 705 that is produced by the reduction of steam can be diverted from the hydrogenation unit 706 and used directly as a fuel source, either alone or in combination with the methane gas. For example, the hydrogen can be directly fired in a boiler, internal combustion engine or fuel cell.

As is discussed above, the primary feedstock to the hydrogenation unit of the present invention can be a low-grade coal as well as a high-grade coal. Indeed, low-grade coal feedstock can be advantageous since they are generally available at a low cost. In one embodiment, the coal feedstock is a low-grade coal having at least 1 weight percent sulfur, more preferably at least about 2 weight percent sulfur. The coal can be pre-treated such as to comminute the coal and remove moisture. For example, it is desirable to comminute the coal to reduce the maximum particle size to not greater than about 1 mm. When the feedstock is comminuted coal, the hydrogenation process results in a highly purified and finely divided carbon product.

The hydrogenation treatment according to the present invention converts the volatiles (e.g., hydrocarbons) in the coal to methane. Preferably, at least about 90 weight percent, more preferably at least about 95 weight percent and even more preferably at least about 99 weight percent of the volatile matter is converted to methane.

As is discussed above, the coal frequently includes contaminants, including high levels of sulfur. The method of the present invention advantageously and simultaneously strips contaminants from the volatile matter fraction of the coal as well as the residual coke. The sulfur, for example, reacts with the hydrogen gas and form hydrogen sulfide, which can be easily removed from the waste stream.

Further, the method of the present invention enables the production of energy from the coal feedstock while producing significantly less carbon dioxide per kilowatt-hour of energy produced than is typically produced in a conventional coal-fired power plant. This lower ratio of carbon dioxide to kilowatt-hours of electricity produced accrues because the method of the present invention converts coal, a solid fuel, to a medium BTU gaseous fuel. The thermal to electric efficiency (expressed as a percentage) for a solid fuel ranges from the mid twenties to the low thirties whereas for a gaseous fuel, the thermal to electric conversion is 55 to 60 percent. The reduction in carbon dioxide emission is an important environmental factor and adds further value to the method.

As is discussed above, the carbon that is produced in the hydrogenation unit can be an activated carbon. Activated carbon is an amorphous form of carbon characterized by high adsorptivity for many gases, vapors and colloidal solids. The internal surface area of the activated carbon exceeds several hundred m$^2$/gram and the density is not greater than about 0.85 g/cm$^3$. Activated carbon has a high value and can be used for air and water purification, waste treatment, removal of mercury (Hg) and SO$_x$ from stack gases and the like. Thus, the hydrogenation process when applied to coal provides a high BTU value gas stream as well as a valuable by-product.

In addition to coal, other hydrocarbon-bearing feedstocks can similarly be treated to produce a valuable product gas that includes methane (CH$_4$). The feedstock is supplied to a hydrogenation unit where it is contacted with large volumes of a gas composition including H$_2$ at an elevated temperature such that a portion of the feedstock converts to CH$_4$.

One advantage of the present invention is that the feedstock can be virtually any hydrocarbon bearing feedstock, including those that are available at a very low or even a negative net cost.

In one embodiment, the feedstock is municipal waste. The municipal waste can include normal household and commercial refuse, hazardous waste, animal waste, sewer sludge, automobile shredder refuse (ASR), scrap rubber tires and the like. Municipal waste is commonly available at a net negative cost since municipalities will typically pay a "tipping" fee for removal and destruction of the waste.

According to the United States Environmental Protection Agency, the United States generated 220 million tons of municipal waste in 1998. The amount of waste per person has steadily increased from 2.7 pounds per person per day in 1960, to 3.7 pounds per person per day in 1980 and about 4.5 pounds per person per day in 1998. The components of the municipal waste (before recycling) in the United States in 1998 according to the EPA are listed in Table 3.

TABLE 3

Average Municipal Waste Composition

| Component | Percentage |
| --- | --- |
| Paper | 38.2% |
| Yard Waste | 12.6% |
| Plastics | 10.2% |
| Food Waste | 10.0% |
| Metals | 7.6% |
| Rubber, Leather and Textiles | 7.0% |
| Glass | 5.7% |
| Wood | 5.4% |
| Other | 3.3% |

When the feedstock is municipal waste, the feedstock can be treated and separated if necessary. For example, magnetic metals such as iron and steel can be easily removed and sold for scrap. Optionally, the cellulose-based materials (e.g., paper and wood) can also be removed from the feedstock to reduce the level of oxygen compounds in the feedstock. For example, air separation can be used to separate this light, relatively dry fraction of the waste that includes, for example, paper and paperboard, yard trimmings and wood. The remaining material, which includes food wastes, plastics, rubber, leather, non-ferrous metals and glass, can be separated by hydraulic classification. The non-ferrous metals and glass can be recycled off-site.

As is discussed above, the term municipal solid waste can include not only residential and general commercial wastes, but specific wastes such as automobile shredder refuse (ASR) or "fluff". ASR, essentially the non-metal components of a recycled automobile, is a heterogeneous mixture of plastics, glass, rubber, fiber, non-recovered metals and dirt. The plastics content of ASR is typically about 20 weight percent and is increasing as the amount of plastic used in automobile construction increases. ASR is presently landfilled and legislation has been proposed in some regions to classify the ASR as a hazardous waste, dramatically increasing the disposal cost. Thus, the conversion of ASR to a useful product gas would enable significant environmental and ecological savings.

Municipal waste, like coal, can be partitioned into volatiles and fixed carbon by the application of heat. The chemical composition of the volatiles driven out of municipal waste can be generically represented as CH$_x$. Thus, the reaction that occurs when the waste is contacted with large volume of hydrogen gas in the hydrogenation unit can be written as:

$$0.5(4-x)H_2 + CH_x \rightarrow CH_4 \tag{9}$$

Advantageously, a large volume of combustible gas is produced from the waste and in accordance with the method of the present invention. About 48,550 cubic feet of gas containing about 19.9 million BTU can be generated from 1 ton of municipal waste. The gas is comprised of about 82 percent carbon monoxide, 16 percent methane and 2 percent hydrogen and contains about 410 BTU per cubic foot.

According to another embodiment, the feedstock can be a hydrocarbon bearing substance such as crude oil, tar sand or a similar substance. Crude oil is a mixture of liquid hydrocarbons that is extracted from the earth's crust for use as fuel and various petroleum products. Because crude oil is a mixture of widely varying constituents and proportions, the physical properties vary widely and many crude oils have a very low value due to contaminants in the oil. The present invention advantageously enables the treatment of such low-grade crude oils to produce a useful gas product.

Tar sand, also called bituminous sand, is a deposit of loose sand or partially consolidated sandstone that is saturated with highly viscous bitumen. Oil recovered from tar sands is commonly referred to as synthetic crude and is a potentially significant form of fossil fuel. The recovery of oil from the tar sand, however, is difficult and costly. The present invention advantageously enables the production of a useful gas product from otherwise low-value tar sand.

It will also be appreciated that a combination of two or more of the above-described components can be used as the feedstock. For example, a separated municipal waste stream can be supplemented with pulverized coal.

Yet another aspect of the present invention is directed to the production of ammonia using hydrogen gas and nitrogen gas as reactants. One of the important aspects of the method according to the present invention is the in-situ manufacture of large quantities of $H_2$ at a relatively low cost. It is believed that one of the primary hindrances to the methods disclosed in the prior art for the production of ammonia is the need for high volumes of hydrogen gas and the high cost associated with the hydrogen gas. According to the present invention, high volumes of hydrogen gas can be economically generated in-situ.

In accordance with the present invention, the nitrogen and hydrogen are combined in a $H_2:N_2$ molar ratio of about 3:1 in order to maximize the production of ammonia ($NH_3$). In a typical ammonia production method, a gas including hydrogen and nitrogen is compressed to about 200 atmospheres of pressure and passed over an iron catalyst at a temperature of from about 380° C. to about 450° C.

Figure 8:
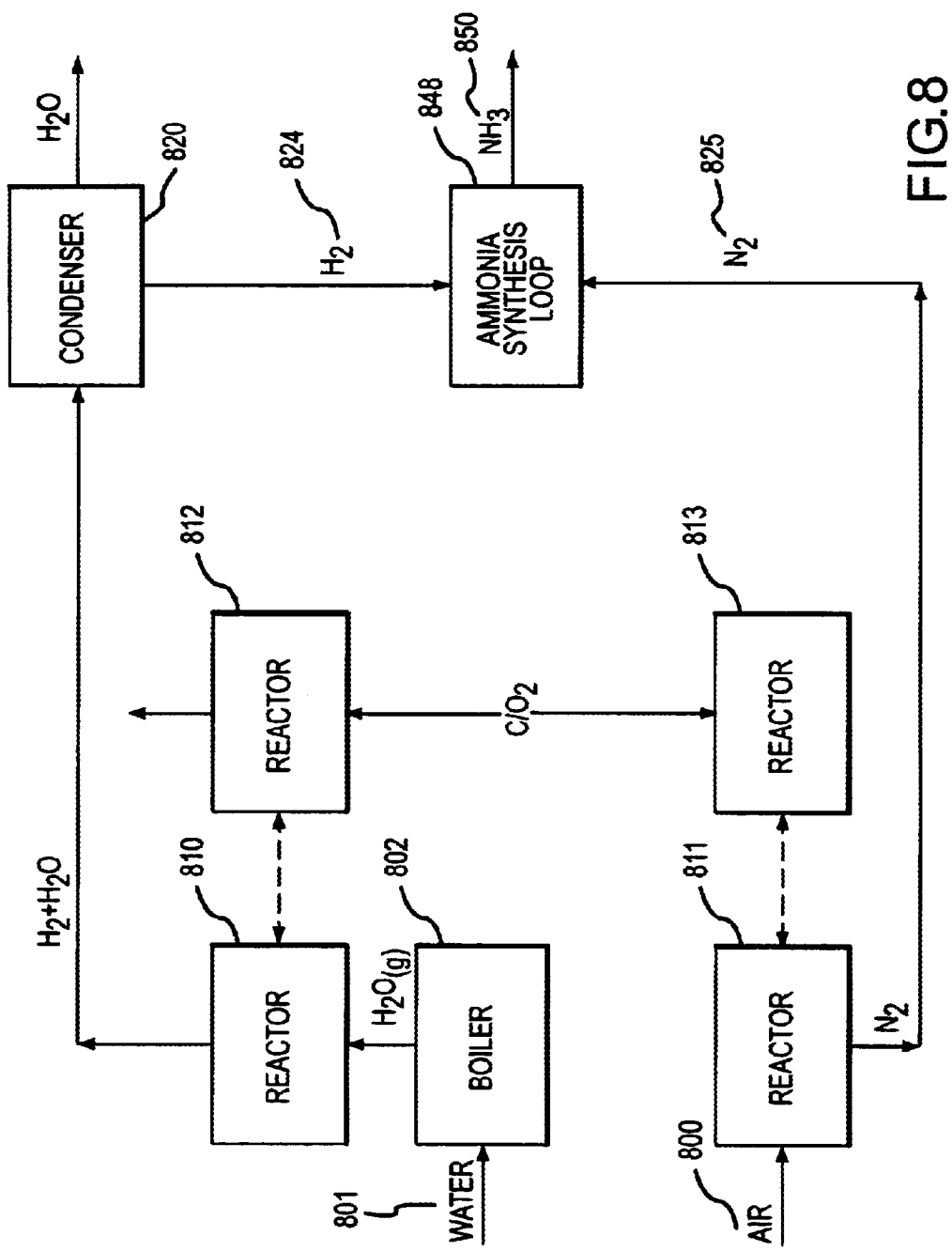
FIG. 8 illustrates a process flow for the production of ammonia according to the present invention.

A method for producing ammonia incorporating the foregoing hydrogen and nitrogen gas production methods is illustrated in FIG. 8. For the production of hydrogen, water 801 is provided to a boiler 802 and steam is provided to one of reactors 810 or 812. The hydrogen gas is then passed to a condenser 820 to remove water and is then supplied to an ammonia synthesis loop 848.

Simultaneously, air 800 is supplied to an oxidation reactor 811 to strip oxygen from the air to provide a nitrogen gas stream 825. In the embodiment illustrated in FIG. 6, the reactor 811 is the metal oxidation reactor whereas the reactor 813 is the metal oxide reduction reactor. Advantageously, a single reactor can be used to provide reduction gas to both the hydrogen production and nitrogen production unit operations.

Thus, hydrogen gas 824 and nitrogen gas 825 are provided to an ammonia synthesis loop 848. The ammonia synthesis loop preferably operates an elevated pressure, such as up to about 200 atmospheres. In addition, the ammonia synthesis loop 848 operates at an elevated temperature and can include a catalyst. The production of ammonia from hydrogen and nitrogen is illustrated in: U.S. Pat. No. 4,600, 571 by McCarroll et al.; U.S. Pat. No. 4,298,588 by Pinto; and U.S. Pat. No. 4,088,740 by Gaines. Each of the foregoing U.S. patents is incorporated herein by reference in their entirety.

The resulting ammonia can be used in a number of applications. For example, the ammonia can be converted to urea for use in fertilizers. The ammonia can also be used to reduce $NO_x$ emissions from coal-fired power plants and for the manufacture of various ammonium-containing compounds.

While various embodiments of the present invention have been described in detail, it is apparent that modifications and adaptations of those embodiments will occur to those skilled in the art. However, it is to be expressly understood that such modifications and adaptations are within the spirit and scope of the present invention.

What is claimed is:

1. A method for the production of a hydrogen-containing gas stream, comprising the steps of:
    a) generating steam;
    b) contacting said steam with a molten metal mixture in a reactor, said molten metal mixture comprising at least about 20 weight percent iron dissolved in a first diluent metal, said first diluent metal being tin and wherein at least a portion of said iron is oxidized to an iron oxide and at least a portion of said steam is reduced to form hydrogen; and
    c) extracting a hydrogen-containing gas stream from said reactor.

2. A method as recited in claim 1, wherein said molten metal mixture further comprises a second reactive metal.

3. A method as recited in claim 1, wherein said molten metal mixture further comprises a second diluent metal.

4. A method as recited in claim 1, wherein solid metallic particles comprising iron are dispersed in said molten metal mixture.

5. A method as recited in claim 4, wherein said molten metal mixture is at a temperature of from about 895° C. to about 1134° C. during said steam contacting step.

6. A method as recited in claim 1, wherein said molten metal mixture is at a temperature that is lower than about 1538° C. during said steam contacting step.

7. A method as recited in claim 1, wherein said molten metal mixture is at a temperature of not greater than about 1400° C. during said steam contacting step.

8. A method as recited in claim 1, wherein said molten metal mixture is at a temperature of from about 1134° C. to about 1300° C. during said steam contacting step.

9. A method as recited in claim 1, wherein said molten metal mixture is at a temperature of from about 1200° C. to about 1300° C. during said steam contacting step.

10. A method as recited in claim 1, wherein said hydrogen-containing gas stream comprises at least about 30 volume percent hydrogen gas.

11. A method as recited in claim 1, further comprising the step of extracting water from said hydrogen-containing gas stream.

12. A method as recited in claim 1, wherein said steam contacting step comprises in injecting steam into said molten metal mixture using a top-submerged lance.

13. A method as recited in claim 1, further comprising the step of contacting said iron oxide with a reductant to reduce said iron oxide back to iron.

14. A method as recited in claim 1, further comprising the step of adding a flux to said molten metal mixture to promote the formation of a slag layer over said molten metal mixture.

15. A method as recited in claim 1, further comprising the step of adding a flux selected from the group consisting of $SiO_2$, FeO, CaO, MgO, $Na_2O$, $K_2O$ and mixtures thereof to said molten metal mixture to promote the formation of a slag layer over said molten metal mixture.

16. A method for the production of a hydrogen-containing gas stream, comprising the steps of:
   a) generating steam;
   b) contacting said steam with a molten metal mixture in a reactor, said molten metal mixture comprising a first reactive metal dissolved in a first diluent metal, wherein said molten metal mixture is at a temperature of at least about 1100° C. and wherein at least a portion of said first reactive metal is oxidized to a first metal oxide and at least a portion of said steam is reduced to form hydrogen; and
   c) extracting said hydrogen-containing gas stream from said reactor.

17. A method as recited in claim 16, wherein said molten metal mixture is at a temperature of at least about 1134° C.

18. A method as recited in claim 16, wherein said molten metal mixture is at a temperature that is lower than the pure melting point of said first reactive metal during said steam contacting step.

19. A method as recited in claim 16, wherein said molten metal mixture is at a temperature of not greater than about 1400° C.

20. A method as recited in claim 16, wherein said molten metal mixture is at a temperature of from about 1200° C. to about 1300° C. during said steam contacting step.

21. A method as recited in claim 16, wherein said molten metal mixture comprises at least about 3 weight percent of said first reactive metal.

22. A method as recited in claim 16, wherein said molten metal mixture comprises at least about 10 weight percent of said first reactive metal.

23. A method as recited in claim 16, wherein said molten metal mixture comprises at least about 20 weight percent of said first reactive metal.

24. A method as recited in claim 16, wherein said first reactive metal is selected from the group consisting of iron, tin, tungsten, germanium, molybdenum, indium, zinc, cobalt and antimony.

25. A method as recited in claim 16, wherein said first reactive metal is iron.

26. A method as recited in claim 16, wherein said molten metal mixture further comprises a second reactive metal.

27. A method as recited in claim 16, wherein said first diluent metal is selected from the group consisting of tin, copper and nickel.

28. A method as recited in claim 16, wherein said diluent metal is tin.

29. A method as recited in claim 16, wherein said molten metal mixture further comprises a second diluent metal.

30. A method as recited in claim 16, wherein said hydrogen-containing gas stream comprises at least about 30 volume percent hydrogen gas.

31. A method as recited in claim 16, further comprising the step of extracting water from said hydrogen-containing gas stream.

32. A method as recited in claim 16, wherein said steam contacting step comprises injecting steam into said molten metal mixture using a top-submerged lance.

33. A method as recited in claim 16, further comprising the step of reducing said first metal oxide back to said reactive metal.

34. A method as recited in claim 16, further comprising the step of adding a flux to said molten metal mixture to promote the formulation of a slag layer.

35. A method as recited in claim 16, further comprising the step of adding a flux selected from the group consisting of $SiO_2$, FeO, CaO, MgO, $Na_2O$, $K_2O$ and mixtures thereof to said molten metal mixture to promote the formation of a slag layer over said molten metal mixture.

36. A method for the production of hydrogen-containing gas stream, comprising the steps of:
   a) generating steam;
   b) contacting said steam with a molten metal mixture in a reactor, said molten metal mixture comprising a first reactive metal dissolved in a first diluent metal and wherein reactive-metal containing particles are dispersed in said molten metal mixture and at least a portion of said first reactive metal dissolved in said diluent metal is oxidized to a first metal oxide and at least a portion of said steam is reduced to form hydrogen; and
   c) extracting said hydrogen-containing gas stream from said reactor,
   wherein said reactive-metal containing particles at least partially dissolve into said molten metal mixture as said first reactive metal is oxidized.

37. A method as recited in claim 36, wherein said first reactive metal is selected from the group consisting of iron, tin, tungsten, germanium, molybdenum, indium, zinc, cobalt and antimony.

38. A method as recited in claim 36, wherein said first reactive metal is iron.

39. A method as recited in claim 36, wherein said molten metal mixture further comprises a second reactive metal.

40. A method as recited in claim 36, wherein said first diluent metal is selected from the group consisting of tin, copper and nickel.

41. A method as recited in claim 36, wherein said first diluent metal is tin.

42. A method as recited in claim 36, wherein said molten metal mixture further comprises a second diluent metal.

43. A method as recited in claim 36, wherein said first reactive metal is iron and said first diluent metal is tin.

44. A method as recited in claim 36, wherein said molten metal mixture is saturated with said first reactive metal.

45. A method as recited in claim 36, wherein said reactive metal containing particles are metallic particles.

46. A method as recited in claim 36, wherein said molten metal mixture is at a temperature of from about 895° C. to about 1134° C. during said steam contacting step.

47. A method as recited in claim 36, wherein said hydrogen-containing gas stream comprises at least about 30 volume percent hydrogen gas.

48. A method as recited in claim 36, wherein said steam contacting step comprises injecting steam into said molten metal mixture using a top-submerged lance.

49. A method as recited in claim 36, further comprising the step of contacting said first metal oxide with a reductant to reduce said first metal oxide back to said first reactive metal.

50. A method as recited in claim 36, further comprising the step of adding a flux to said molten metal mixture to promote the formation of a slag layer over said molten metal mixture.

51. A method as recited in claim 36, further comprising the step of adding a flux selected from the group consisting of $SiO_2$, FeO, CaO, MgO, $Na_2O$, $K_2O$ and mixtures thereof to said molten metal mixture to promote the formation of a slag layer over said molten metal mixture.

52. A method for the production of a hydrogen-containing gas stream, comprising the steps of:

a) generating steam;
b) contacting said steam with a molten metal mixture in a reactor, said molten metal mixture comprising molten iron dissolved in molten tin wherein said steam reacts with said molten iron to form hydrogen and iron oxide; and
c) extracting a hydrogen-containing gas stream from said reactor.

53. A method as recited in claim 52, wherein said molten metal mixture is at a temperature of at least about 1134° C. during said steam contacting step.

54. A method as recited in claim 52, wherein said molten metal mixture is at a temperature of not greater than about 1400° C. during said steam contacting step.

55. A method as recited in claim 52, wherein said molten metal mixture is at a temperature of from about 1200° C. to about 1300° C. during said steam contacting step.

56. A method as recited in claim 52, wherein said molten metal mixture comprises at least about 3 weight percent of said molten iron dissolved in said molten tin.

57. A method as recited in claim 52, wherein said molten metal mixture comprises at least about 10 weight percent molten iron dissolved in said molten tin.

58. A method as recited in claim 52, wherein said contacting step comprises injecting steam into said molten metal mixture using a top-submerged lance.

59. A method as recited in claim 52, wherein iron-containing particles are dispersed in said molten metal mixture and wherein iron from said iron-containing particles dissolves into said molten metal mixture as said steam reacts with said molten iron.

60. A method as recited in claim 59, wherein said molten metal mixture is at a temperature of from about 895° C. to about 1134° C. during said steam contacting step.

61. A method as recited in claim 52, wherein said hydrogen-containing gas stream comprises at least about 30 volume percent hydrogen.

62. A method as recited in claim 52, further comprising the step of extracting water from said hydrogen-containing gas stream.

63. A method for the production of hydrogen gas, comprising the steps of:
a) contacting steam with a molten metal mixture in a reactor, said molten metal mixture comprising a first molten reactive metal dissolved in a first molten diluent metal to oxidize at least a portion of said first reactive metal to a first metal oxide and form a hydrogen-containing gas stream;
b) extracting said hydrogen-containing gas stream; and
c) reducing said first metal oxide within said reactor back to said first reactive metal by injecting particulate carbon and an oxygen-containing gas into said reactor.

64. A method as recited in claim 63, wherein said reducing step comprises injecting coal and an oxygen-containing gas into said reactor.

65. A method as recited in claim 63, wherein said reducing step comprises injecting coal and an oxygen-containing gas into said reactor through a submerged lance.

66. A method as recited in claim 63, wherein said first reactive metal is iron.

67. A method as recited in claim 63, wherein said first diluent metal is tin.

68. A method as recited in claim 63, wherein said first reactive metal is iron and said diluent metal is tin.

69. A method as recited in claim 63, wherein said molten metal mixture has a temperature of at least about 1134° C. during said steam contacting step.

70. A method as recited in claim 63, wherein said molten metal mixture has a temperature of from about 1200° C. to about 1300° C. during said steam contacting step.

71. A method as recited in claim 63, wherein said steam contacting step comprises injecting steam into said molten metal mixture using a top-submerged lance.

72. A method as recited in claim 63, further comprising the step of adding a flux to said molten metal mixture to promote the formation of a slag layer.

73. A method as recited in claim 63, further comprising the step of adding a flux selected from the group consisting of $SiO_2$, FeO, CaO, MgO, $Na_2O$ and $K_2O$ to said molten metal mixture to promote the formation of a slag layer.

74. A method for the production of a hydrogen-containing gas stream, comprising the steps of:
a) generating steam;
b) injecting said steam into a molten metal mixture contained in a reactor, said molten metal mixture comprising molten iron dissolved in molten tin under conditions sufficient to form a hydrogen-containing gas stream and a slag layer comprising iron oxide on top of said molten metal mixture;
c) extracting said hydrogen-containing gas stream from said reactor;
d) ceasing said injection of steam; and
e) injecting a particulate carbon source and an oxygen-containing gas into said reactor to reduce said iron oxide to iron metal.

75. A method as recited in claim 74, wherein said molten metal mixture has a temperature of at least about 1134° C.

76. A method as recited in claim 74, wherein said steam injection step comprises injecting steam using a top-submerged lance.

77. A method as recited in claim 74, wherein said step of injecting a carbon source comprises injecting coal into said reactor.

78. A method as recited in claim 74, further comprising the step of adding a flux to said molten metal mixture to promote the formation of said slag layer.

79. A method as recited in claim 74, further comprising the step of adding a flux selected from the group consisting of $SiO_2$, FeO, CaO, MgO, $Na_2O$ and $K_2O$ to said molten metal mixture to promote the formation of said slag layer.

80. A method for the production of a hydrogen-containing gas stream, comprising the steps of:
a) generating steam;
b) injecting said steam into a molten metal mixture contained in a reactor, said molten metal mixture comprising a first molten metal dissolved in a second molten metal, wherein said steam reacts with said first molten metal to form hydrogen and a first metal oxide having a density that is at least about 10 percent less than said molten metal mixture, whereby said first metal oxide rises in said molten metal mixture to a slag layer disposed above said molten metal mixture; and
c) extracting a hydrogen-containing gas from said reactor.

81. A method as recited in claim 80, wherein said first molten metal is iron.

82. A method as recited in claim 80, wherein said second molten metal is tin.

83. A method as recited in claim 80, further comprising the steps of:
d) terminating said injection of steam; and
e) reducing said first metal oxide in said slag layer to said first molten metal wherein said first molten metal redissolves in said molten metal mixture.

84. A method for the treatment of coal, comprising the steps of:
  a) generating a hydrogen-containing gas stream by a method comprising the steps of:
    i) generating steam;
    ii) injecting said steam into a molten metal mixture contained in a first reactor, said molten metal mixture comprising molten iron dissolved in molten tin under conditions sufficient to oxidize a portion of said molten iron to iron oxide and form a hydrogen-containing gas stream; and
    iii) extracting said hydrogen-containing gas stream from said first reactor;
  b) contacting said hydrogen-containing gas stream with particulate coal in a second reactor at a temperature of at least about 700° C.; and
  c) extracting a methane-containing gas stream from said second reactor.

85. A method as recited in claim 84, further comprising the step of extracting a coke product from said second reactor.

86. A method as recited in claim 84, further comprising the step of extracting a coke product from said second reactor and injecting said coke product into said first reactor to reduce said iron oxide to iron.

87. A method for the production of ammonia, comprising the steps of:
  a) generating a hydrogen-containing gas stream by a method comprising the steps of:
    i) generating steam;
    ii) injecting said steam into a molten metal mixture contained in a first reactor, said molten metal mixture comprising molten iron dissolved in molten tin under conditions sufficient to oxidize a portion of said molten iron to iron oxide form a hydrogen-containing gas stream; and
    iii) extracting said hydrogen-containing gas stream from said first reactor; and
  b) contacting said hydrogen-containing gas stream with a nitrogen-containing gas stream to form ammonia.

* * * * *

UNITED STATES PATENT AND TRADEMARK OFFICE
CERTIFICATE OF CORRECTION

PATENT NO. : 6,663,681 B2 Page 1 of 1
DATED : December 16, 2003
INVENTOR(S) : Kindig et al.

It is certified that error appears in the above-identified patent and that said Letters Patent is hereby corrected as shown below:

Column 6,
Line 24, delete the word "metal-contaning", and insert therefor -- metal-containing --.

Column 22,
Line 58, delete the word "in".

Signed and Sealed this

Ninth Day of March, 2004

JON W. DUDAS
*Acting Director of the United States Patent and Trademark Office*